US009125567B2

(12) United States Patent
Gross et al.

(10) Patent No.: US 9,125,567 B2
(45) Date of Patent: Sep. 8, 2015

(54) DEVICES AND METHODS FOR CONTROL OF BLOOD PRESSURE

(75) Inventors: Yossi Gross, Moshav Mazor (IL); Itzik Avneri, Tel Aviv (IL); Omry Ben Ezra, Tel Aviv (IL); Ori Weisberg, Shdema (IL); Raanan Gefen, Reut (IL)

(73) Assignee: VASCULAR DYNAMICS, INC., Mountain View, CA (US)

( * ) Notice: Subject to any disclaimer, the term of this patent is extended or adjusted under 35 U.S.C. 154(b) by 293 days.

(21) Appl. No.: 12/602,787

(22) PCT Filed: Sep. 29, 2009

(86) PCT No.: PCT/IL2009/000932
§ 371 (c)(1),
(2), (4) Date: May 17, 2011

(87) PCT Pub. No.: WO2010/035271
PCT Pub. Date: Apr. 1, 2010

(65) Prior Publication Data
US 2011/0213408 A1  Sep. 1, 2011

Related U.S. Application Data

(60) Provisional application No. 61/194,339, filed on Sep. 26, 2008.

(51) Int. Cl.
*A61B 17/00* (2006.01)
*A61B 5/021* (2006.01)
(Continued)

(52) U.S. Cl.
CPC ............... *A61B 5/021* (2013.01); *A61B 5/6862* (2013.01); *A61B 5/6876* (2013.01); *A61B 5/022* (2013.01)

(58) Field of Classification Search
CPC .... A61B 5/021; A61B 5/6876; A61B 5/6862; A61B 5/022; A61B 5/0215; A61F 2/06; A61F 5/0079; A61F 2250/0059; A61F 2230/0045; A61F 2/856
USPC ............... 623/1.11, 1.15, 1.16; 604/201–204; 607/44; 600/17
See application file for complete search history.

(56) References Cited

U.S. PATENT DOCUMENTS

| 3,650,277 A | 3/1972 | Sjostrand et al. |
| 4,201,219 A | 5/1980 | Gonzalez et al. |

(Continued)

FOREIGN PATENT DOCUMENTS

| EP | 0791341 A1 | 8/1997 |
| EP | 1127557 A1 | 8/2001 |

(Continued)

OTHER PUBLICATIONS

International search report and written opinion dated Dec. 5, 2012 for PCT/IL2011/000356.

(Continued)

*Primary Examiner* — Katrina Stransky
(74) *Attorney, Agent, or Firm* — Wilson Sonsini Goodrich & Rosati

(57) ABSTRACT

Apparatus is provided for reducing hypertension of a subject. A selective circumferential pressure applicator (60) includes at least two surfaces (61) that increase baroreceptor activity of the subject, by applying pressure to an artery (20) of the subject at two or more respective non-contiguous regions around the circumference of the artery, at a longitudinal site of the artery, such that between the non-contiguous regions, at the longitudinal site (a) there is at least one region (22) of the artery that is more relaxed than in the absence of the device, and (b) there is at least one region (21) of the artery that is more tense than in the absence of the device. A joint (63) couples the surfaces to each other. For at least a portion of the subject's cardiac cycle, the joint does not to contact the subject's artery. Other applications are also provided.

20 Claims, 12 Drawing Sheets

(51) Int. Cl.
*A61B 5/00* (2006.01)
*A61B 5/022* (2006.01)

(56) References Cited

U.S. PATENT DOCUMENTS

| | | | |
|---|---|---|---|
| 4,791,931 A | 12/1988 | Slate | |
| 4,830,003 A | 5/1989 | Wolff et al. | |
| 4,938,766 A | 7/1990 | Jarvik | |
| 5,403,341 A | 4/1995 | Solar | |
| 5,437,285 A | 8/1995 | Verrier et al. | |
| 5,458,626 A | 10/1995 | Krause | |
| 5,630,829 A | 5/1997 | Lauterjung | |
| 5,669,924 A | 9/1997 | Shaknovich | |
| 5,707,400 A | 1/1998 | Terry, Jr. et al. | |
| 5,727,558 A | 3/1998 | Hakki et al. | |
| 5,792,155 A | 8/1998 | Van Cleef | |
| 6,013,085 A | 1/2000 | Howard | |
| 6,086,527 A | 7/2000 | Talpade | |
| 6,306,141 B1 | 10/2001 | Jervis | |
| 6,322,553 B1 | 11/2001 | Vito | |
| 6,375,666 B1 | 4/2002 | Mische | |
| 6,413,273 B1 | 7/2002 | Baum et al. | |
| 6,442,424 B1 | 8/2002 | Ben-Haim et al. | |
| 6,520,987 B1 | 2/2003 | Plante | |
| 6,522,926 B1 | 2/2003 | Kieval et al. | |
| 6,554,856 B1 | 4/2003 | Doorly et al. | |
| 6,575,994 B1 | 6/2003 | Marin et al. | |
| 6,616,624 B1 | 9/2003 | Kieval | |
| 6,641,605 B1 | 11/2003 | Stergiopulos | |
| 6,669,686 B1 | 12/2003 | Singh | |
| 6,681,136 B2 | 1/2004 | Schuler et al. | |
| 6,764,498 B2 | 7/2004 | Mische | |
| 6,850,801 B2 | 2/2005 | Kieval et al. | |
| 6,899,669 B2 | 5/2005 | Vito et al. | |
| 6,957,106 B2 | 10/2005 | Schuler et al. | |
| 6,972,031 B1 | 12/2005 | Braginsky et al. | |
| 6,974,445 B2 | 12/2005 | Stergiopulos | |
| 6,985,774 B2 | 1/2006 | Kieval et al. | |
| 7,008,446 B1 | 3/2006 | Amis et al. | |
| 7,044,981 B2 | 5/2006 | Liu et al. | |
| 7,060,080 B2 | 6/2006 | Bachmann | |
| 7,094,254 B2 | 8/2006 | Stergiopulos | |
| 7,128,750 B1 | 10/2006 | Stergiopulos | |
| 7,158,832 B2 | 1/2007 | Kieval et al. | |
| 7,159,593 B2 | 1/2007 | McCarthy et al. | |
| 7,194,313 B2 | 3/2007 | Libbus | |
| 7,201,772 B2 | 4/2007 | Schwammenthal et al. | |
| 7,218,964 B2 | 5/2007 | Hill et al. | |
| 7,238,191 B2 | 7/2007 | Bachmann | |
| 7,270,675 B2 | 9/2007 | Chun et al. | |
| 7,300,449 B2 | 11/2007 | Mische | |
| 7,331,987 B1 | 2/2008 | Cox | |
| 7,373,204 B2 | 5/2008 | Gelfand et al. | |
| 7,381,222 B2 | 6/2008 | Pflueger et al. | |
| 7,389,149 B2 | 6/2008 | Rossing et al. | |
| 7,395,119 B2 | 7/2008 | Hagen et al. | |
| 7,491,229 B2 | 2/2009 | Eder et al. | |
| 7,530,995 B2 | 5/2009 | Quijano et al. | |
| 7,625,400 B2 | 12/2009 | Bowe et al. | |
| 7,628,803 B2 | 12/2009 | Pavcnik et al. | |
| 7,637,937 B2 | 12/2009 | Case et al. | |
| 7,647,931 B2 | 1/2010 | Pflueger et al. | |
| 8,361,140 B2 | 1/2013 | Meyer et al. | |
| 8,923,972 B2 | 12/2014 | Gross | |
| 2001/0003801 A1 | 6/2001 | Strecker | |
| 2002/0035392 A1 | 3/2002 | Wilson | |
| 2002/0173838 A1 | 11/2002 | Frazier | |
| 2003/0060585 A1 | 3/2003 | Radhakrishnan et al. | |
| 2003/0060858 A1 | 3/2003 | Kieval et al. | |
| 2003/0199806 A1 | 10/2003 | Kieval | |
| 2004/0010303 A1 | 1/2004 | Bolea et al. | |
| 2004/0019364 A1 | 1/2004 | Kieval et al. | |
| 2004/0106976 A1 | 6/2004 | Bailey et al. | |
| 2004/0111006 A1 | 6/2004 | Alferness et al. | |
| 2004/0149294 A1 | 8/2004 | Gianchandani et al. | |
| 2004/0193092 A1 | 9/2004 | Deal | |
| 2004/0249442 A1 | 12/2004 | Fleming et al. | |
| 2004/0254616 A1 | 12/2004 | Rossing et al. | |
| 2005/0027346 A1 | 2/2005 | Arkusz et al. | |
| 2005/0033407 A1 | 2/2005 | Weber et al. | |
| 2005/0090894 A1 | 4/2005 | Pazienza et al. | |
| 2005/0096710 A1 | 5/2005 | Kieval | |
| 2005/0143765 A1 | 6/2005 | Bachmann et al. | |
| 2005/0143766 A1 | 6/2005 | Bachmann et al. | |
| 2005/0143785 A1 | 6/2005 | Libbus | |
| 2005/0149128 A1 | 7/2005 | Heil et al. | |
| 2005/0149131 A1 | 7/2005 | Libbus et al. | |
| 2005/0149143 A1 | 7/2005 | Libbus et al. | |
| 2005/0154418 A1 | 7/2005 | Kieval et al. | |
| 2005/0203610 A1 | 9/2005 | Tzeng | |
| 2005/0232965 A1 | 10/2005 | Falotico | |
| 2005/0251212 A1 | 11/2005 | Kieval et al. | |
| 2005/0261257 A1 | 11/2005 | Vermeer | |
| 2006/0004417 A1 | 1/2006 | Rossing et al. | |
| 2006/0004420 A1 | 1/2006 | Rossing et al. | |
| 2006/0004430 A1 | 1/2006 | Rossing et al. | |
| 2006/0074453 A1 | 4/2006 | Kieval et al. | |
| 2006/0089678 A1 | 4/2006 | Shalev | |
| 2006/0111626 A1 | 5/2006 | Rossing et al. | |
| 2006/0217588 A1 | 9/2006 | Gross et al. | |
| 2006/0241334 A1 | 10/2006 | Dubi et al. | |
| 2006/0253193 A1 | 11/2006 | Lichtenstein et al. | |
| 2006/0265038 A1 | 11/2006 | Hagen et al. | |
| 2006/0276852 A1 | 12/2006 | Demarais et al. | |
| 2006/0293712 A1 | 12/2006 | Kieval et al. | |
| 2007/0021790 A1 | 1/2007 | Kieval et al. | |
| 2007/0021792 A1 | 1/2007 | Kieval et al. | |
| 2007/0021794 A1 | 1/2007 | Kieval et al. | |
| 2007/0021796 A1 | 1/2007 | Kieval et al. | |
| 2007/0021797 A1 | 1/2007 | Kieval et al. | |
| 2007/0021798 A1 | 1/2007 | Kieval et al. | |
| 2007/0021799 A1 | 1/2007 | Kieval et al. | |
| 2007/0038255 A1 | 2/2007 | Kieval et al. | |
| 2007/0038259 A1 | 2/2007 | Kieval et al. | |
| 2007/0038260 A1 | 2/2007 | Kieval et al. | |
| 2007/0038261 A1 | 2/2007 | Kieval et al. | |
| 2007/0038262 A1* | 2/2007 | Kieval et al. ............ 607/44 |
| 2007/0049989 A1 | 3/2007 | Rossing et al. | |
| 2007/0055296 A1 | 3/2007 | Stergiopulos | |
| 2007/0060972 A1 | 3/2007 | Kieval et al. | |
| 2007/0100433 A1 | 5/2007 | Limon | |
| 2007/0106340 A1 | 5/2007 | Bolea et al. | |
| 2007/0142879 A1 | 6/2007 | Greenberg et al. | |
| 2007/0156167 A1 | 7/2007 | Connors et al. | |
| 2007/0156198 A1 | 7/2007 | Rossing et al. | |
| 2007/0156201 A1 | 7/2007 | Rossing | |
| 2007/0167984 A1 | 7/2007 | Kieval et al. | |
| 2007/0185542 A1 | 8/2007 | Bolea et al. | |
| 2007/0185543 A1 | 8/2007 | Rossing et al. | |
| 2007/0187255 A1 | 8/2007 | Ogasawara et al. | |
| 2007/0198082 A1 | 8/2007 | Kapadia et al. | |
| 2007/0250085 A1 | 10/2007 | Bachmann et al. | |
| 2007/0276442 A1 | 11/2007 | Hagen et al. | |
| 2007/0276459 A1 | 11/2007 | Rossing et al. | |
| 2007/0282385 A1 | 12/2007 | Rossing et al. | |
| 2007/0287879 A1 | 12/2007 | Gelbart et al. | |
| 2008/0004673 A1 | 1/2008 | Rossing et al. | |
| 2008/0009916 A1 | 1/2008 | Rossing et al. | |
| 2008/0009917 A1 | 1/2008 | Rossing et al. | |
| 2008/0027469 A1 | 1/2008 | Bachmann | |
| 2008/0033501 A1 | 2/2008 | Gross | |
| 2008/0046054 A1 | 2/2008 | Hjelle et al. | |
| 2008/0051767 A1 | 2/2008 | Rossing et al. | |
| 2008/0082137 A1 | 4/2008 | Kieval et al. | |
| 2008/0097540 A1 | 4/2008 | Bolea et al. | |
| 2008/0114439 A1 | 5/2008 | Ramaiah et al. | |
| 2008/0132966 A1 | 6/2008 | Levin et al. | |
| 2008/0140167 A1 | 6/2008 | Hagen | |
| 2008/0154349 A1 | 6/2008 | Rossing et al. | |
| 2008/0161865 A1 | 7/2008 | Hagen | |
| 2008/0161887 A1 | 7/2008 | Hagen | |
| 2008/0167690 A1 | 7/2008 | Cody et al. | |
| 2008/0167693 A1 | 7/2008 | Kieval et al. | |
| 2008/0167694 A1 | 7/2008 | Bolea et al. | |

(56) References Cited

U.S. PATENT DOCUMENTS

| | | |
|---|---|---|
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0181927 A1 | 7/2008 | Zhao |
| 2008/0194905 A1 | 8/2008 | Walsh |
| 2008/0195190 A1* | 8/2008 | Bland et al. .................. 623/1.11 |
| 2008/0275539 A1 | 11/2008 | Williams et al. |
| 2008/0319504 A1 | 12/2008 | Loushin et al. |
| 2009/0248138 A1 | 10/2009 | Golesworthy et al. |
| 2009/0248141 A1 | 10/2009 | Shandas et al. |
| 2009/0264914 A1 | 10/2009 | Riina et al. |
| 2009/0292348 A1 | 11/2009 | Berez et al. |
| 2009/0306756 A1 | 12/2009 | Cho et al. |
| 2010/0211131 A1 | 8/2010 | Williams et al. |
| 2011/0077729 A1 | 3/2011 | Gross |
| 2011/0178416 A1 | 7/2011 | Gross |
| 2011/0230953 A1 | 9/2011 | Gross |
| 2011/0230957 A1 | 9/2011 | Bonsignore et al. |
| 2013/0172981 A1 | 7/2013 | Gross et al. |
| 2014/0135902 A1 | 5/2014 | Gross et al. |

FOREIGN PATENT DOCUMENTS

| | | |
|---|---|---|
| EP | 1153580 A1 | 11/2001 |
| EP | 1153581 A1 | 11/2001 |
| EP | 1200152 A1 | 5/2002 |
| EP | 1234554 A1 | 8/2002 |
| EP | 1343112 A1 | 9/2003 |
| EP | 1483730 A1 | 12/2004 |
| WO | WO-0105463 A1 | 1/2001 |
| WO | WO 01/85063 A1 | 11/2001 |
| WO | WO-0226314 A1 | 4/2002 |
| WO | WO 03/077191 A1 | 9/2003 |
| WO | WO-03076008 A1 | 9/2003 |
| WO | WO-03082080 A2 | 10/2003 |
| WO | WO-03082403 A2 | 10/2003 |
| WO | WO-2004073484 A2 | 9/2004 |
| WO | WO 2005/021063 A2 | 3/2005 |
| WO | WO 2005/065771 A1 | 7/2005 |
| WO | WO-2005084389 A2 | 9/2005 |
| WO | WO-2005097256 A2 | 10/2005 |
| WO | WO 2005/021063 A3 | 2/2006 |
| WO | WO-2006012033 A2 | 2/2006 |
| WO | WO-2006012050 A2 | 2/2006 |
| WO | WO-2006032902 A1 | 3/2006 |
| WO | WO-2006040647 A1 | 4/2006 |
| WO | WO-2006041664 A2 | 4/2006 |
| WO | WO 2006042280 A2 * | 4/2006 |
| WO | WO-2006125163 A2 | 11/2006 |
| WO | WO-2007013065 A2 | 2/2007 |
| WO | WO-2007047152 A2 | 4/2007 |
| WO | WO-2007080595 A2 | 7/2007 |
| WO | WO-2007114860 A2 | 10/2007 |
| WO | WO-2007118090 A2 | 10/2007 |
| WO | WO-2007136850 A2 | 11/2007 |
| WO | WO-2007136851 A2 | 11/2007 |
| WO | WO-2008039982 A2 | 4/2008 |
| WO | WO-2008083120 A2 | 7/2008 |
| WO | WO-2008083235 A2 | 7/2008 |
| WO | WO-2009018394 A1 | 2/2009 |
| WO | WO 2010/035271 A1 | 4/2010 |
| WO | WO 2011/089601 A1 | 7/2011 |

OTHER PUBLICATIONS

U.S. Appl. No. 13/455,005, filed Apr. 24, 2012, Gross et al.
B. Ziaie, et al, "An Implantable Pressure Sensor Cuff for Tonometric Blood Pressure Measurement," IEEE Solid-State Sensor and Actuator Worksho., pp. 216-219, Jun. 1998.
Mendelsohn (1998). Acute Hemodynamic Changes During Carotid Artery Stenting. Am J Cardiol 82:1077-1081.
Riley W. A. Barnes R. W. Evans G W Burke G L Evans Gregory W & Burke Gregory L. (1992). Ultrasonic measurement of the elastic modulus of the common carotid artery. The Atherosclerosis Risk in Communities (ARIC) Study WA Riley RW Barnes GW Evans and GL Burke Stroke 1992;23:952-956. *Stroke.*
Delfino A. Stergiopulos N. & Moore J. E. (1997). Residual Strain Effects on the Stress Field in a Thick Wall Finite Element Model of the Human Carotid Bifurcation. *Science* 30(8) 777-786.
Mendelowitz D. & Scher a M. (1990). Pulsatile pressure can prevent rapid baroreflex resetting. *The American journal of physiology* 258(1 Pt 2) H92-100. Retrieved from http:www.ncbi.nlm.nih. govpubmed2301618.
Office action dated Jan. 3, 2013 for U.S. Appl. No. 12/774,254.
Office action dated Mar. 14, 2013 for U.S. Appl. No. 13/030,384.
Office action dated Apr. 19, 2012 for U.S. Appl. No. 12/774,254.
Office action dated Sep. 27, 2012 for U.S. Appl. No. 13/030,384.
U.S. Appl. No. 14/092,433, filed Nov. 27, 2013, Gross et al.
U.S. Appl. No. 14/560,194, filed Dec. 4, 2014, Gross.
U.S. Appl. No. 60/702,491, filed Jul. 25, 2005, Gross.
U.S. Appl. No. 60/721,728, filed Sep. 28, 2005, Gross.
Davos. The effect of baroreceptor activity on cardiovascular regulation. Hellenic J. cardiol. 2002; 43:145-155.
European search report and opinion dated Dec. 14, 2012 for EP Application No. 06766171.
International search report and written opinion dated Jan. 24, 2007 for PCT/IL2006/000856.
Notice of Allowance dated Nov. 20, 2014 for U.S. Appl. No. 11/881,256.
Office action dated Jan. 14, 2013 for U.S. Appl. No. 11/881,256.
Office action dated May 24, 2012 for U.S. Appl. No. 11/881,256.
Office action dated Jun. 23, 2014 for U.S. Appl. No. 11/881,256.
Office action dated Oct. 21, 2014 for U.S. Appl. No. 13/116,370.
Office action dated Nov. 5, 2014 for U.S. Appl. No. 11/881,256.
J.H.P. Lardenoye, et al., "Inhibition of Accelerated Atherosclerosis in Vein Grafts by Placement of External Stent in ApoE*3-Leiden Transgenic Mice", Arteriosclerosis, Thrombosis, and Vascular Biology. 2002; 22:1433.) © 2002.
An International Search Report dated Feb. 3, 2010, which issued during the prosecution of Applicant's PCT/M09/00932.
"The effects of altering mean pressure, pulse pressure and pulse frequency on the impulse activity in baroreceptor fibres from the aortic arch and right subclavian artery in the rabbit," Angell James JE, J Physiol. Apr. 1971; 214(1):65-88.
"Theoretical and electrophysiological evidence for axial loading about aortic baroreceptor nerve terminals in rats," Feng B, Am J Physiol Heart Circ Physiol. Dec. 2007; 293(6):H3659-72.
"Ascorbic Acid Selectively Improves Large Elastic Artery Compliance in Postmenopausal Women," Moreau K.L., Hypertension 2005;45: 1107.
"Carotid sinus nerve blockade to reduce blood pressure instability following carotid endarterectomy: a systematic review and meta-analysis," Tang T.Y., Eur J Vase Endovasc Surg. Sep. 2007; 34(3):304-11, (an abstract).
"Coronary artery baroreceptor-mediated changes in arterial pressure: a pilot study in conscious and anaesthetized sheep," Bennetts J.S., Clin Exp Pharmacol Physiol. Sep. 2001; 28(9):768-72, (an abstract).
"Effect of increased renal venous pressure on renal function," Doty J. M., The Journal of Trauma: Injury, Infection, and Critical Care: Dec. 1999, vol. 47, Issue 6, p. 1000, (an abstract).
"Glomerular ultrafiltration dynamics during increased renal venous pressure," J.R. Dilley, AJP—Renal Physiology, vol. 244, Issue 6 650-F658 (an abstract), 1983.
"Implantable penile venous compression device: initial experience in the acute canine model," Paick J., The Journal of Urology 1992, vol. 148, No. 1, pp. 188-191, (an abstract).
S. Levenberg, et al., "Endothelial cells derived from human embryonic stem cells", PNAS Apr. 2, 2002, vol. 99, No. 7 pp. 4391-4396.
Office action dated Jan. 2, 2015 for U.S. Appl. No. 13/455,005.
Office action dated Dec. 4, 2014 for U.S. Appl. No. 13/030,384.

\* cited by examiner

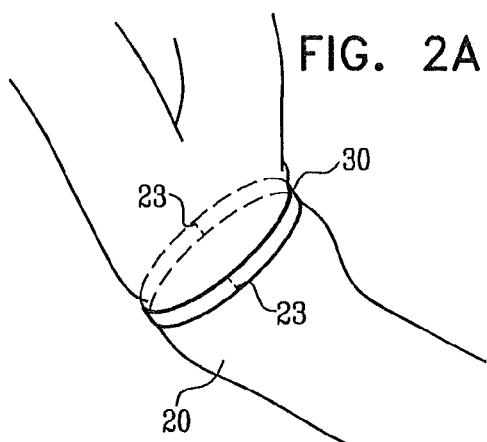
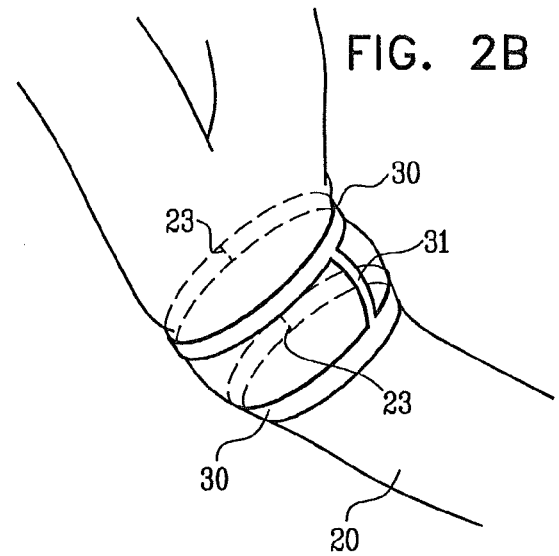
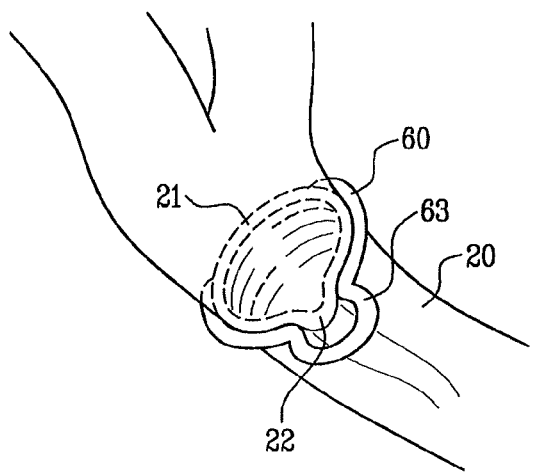
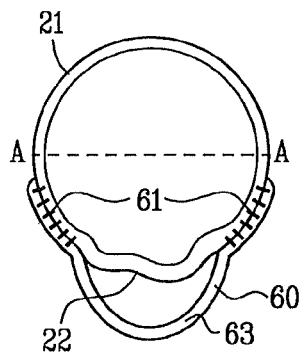
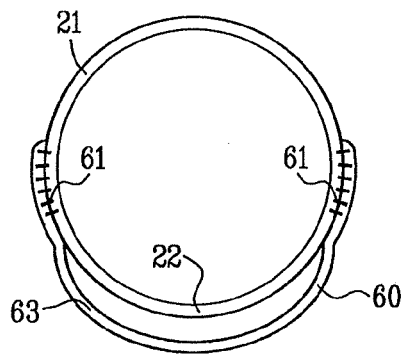

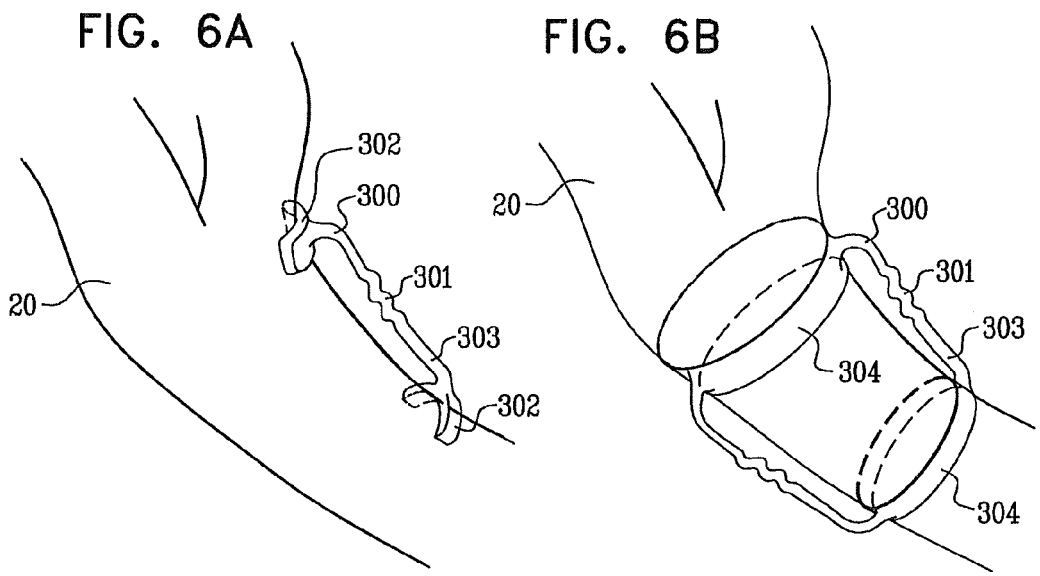
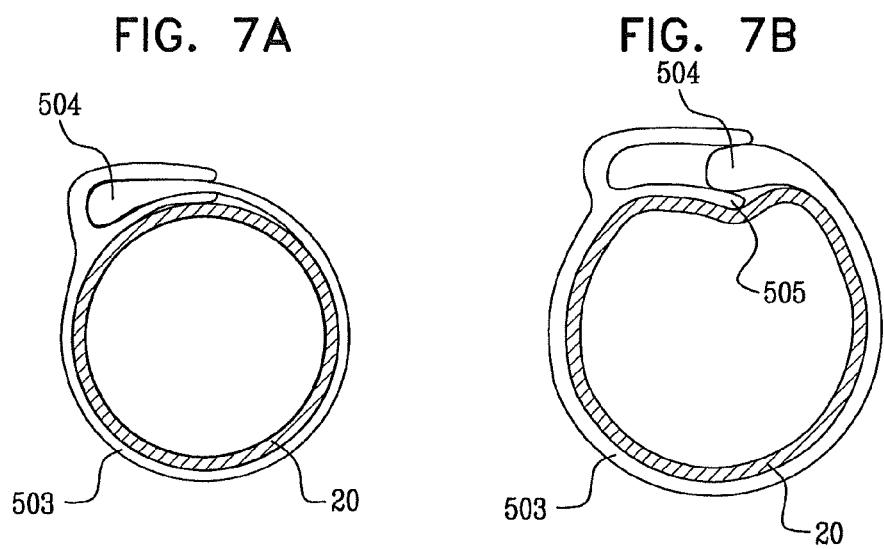

US 9,125,567 B2

DEVICES AND METHODS FOR CONTROL OF BLOOD PRESSURE

CROSS-REFERENCES TO RELATED APPLICATIONS

The present patent application is a U.S. national phase of PCT Application no. PCT/IL2009/000932 to Gross et al., filed Sep. 29, 2009, which claims priority from U.S. Patent Application 61/194,339, filed Sep. 26, 2008, entitled "Devices and methods for control of blood pressure," each of which is incorporated herein by reference in its entirety.

The present patent application is related to U.S. patent application Ser. No. 11/881,256 (U.S. 2008/0033501), filed Jul. 25, 2007, entitled "Elliptical element for blood pressure reduction," which is a continuation-in-part of International Patent Application PCT/IL2006/000856 to Gross (WO 07/013065), filed Jul. 25, 2006, entitled, "Electrical stimulation of blood vessels," which claims the benefit of (a) U.S. Provisional Application No. 60/702,491, filed Jul. 25, 2005, entitled, "Electrical stimulation of blood vessels," and (b) U.S. Provisional Application No. 60/721,728, filed Sep. 28, 2005, entitled, "Electrical stimulation of blood vessels."

All of the above applications are incorporated herein by reference.

FIELD OF THE INVENTION

Applications of the present invention generally relate to implanted medical apparatus. Specifically, applications of the present invention relate to apparatus and methods for reducing blood pressure.

BACKGROUND OF THE INVENTION

Hypertension is a condition from which many people suffer. It is a constant state of elevated blood pressure which can be caused by a number of factors, for example, genetics, obesity or diet. Baroreceptors located in the walls of blood vessels act to regulate blood pressure. They do so by sending information to the central nervous system (CNS) regarding the extent to which the blood vessel walls are stretched by the pressure of the blood flowing therethrough. In response to these signals, the CNS adjusts certain parameters so as to maintain a stable blood pressure.

U.S. Patent Application Publication 2008/0033501 to Gross describes apparatus for treating hypertension of a subject. The apparatus includes an implantable element which has a non-circular shape and which is configured to reduce the hypertension by facilitating an assumption of a non-circular shape by a blood vessel in a vicinity of a baroreceptor of the subject, during diastole of the subject. Other embodiments are also described.

CVRx (Minneapolis, Minn.) manufactures the CVRx® Rheos Baroreflex Hypertension Therapy System, an implantable medical device for treating subjects with high blood pressure.

The following references may be of interest:

European Patent 0,791,341 to Demeyere et al.,

PCT Publication WO 02/26314 to Kieval, PCT Publication WO 03/076008 to Shalev, PCT Publication WO 03/082080 to Bolea, PCT Publication WO 03/082403 to Kieval, PCT Publication WO 04/073484 to Gross et al., PCT Publication WO 05/084389 to Kieval, PCT Publication WO 05/097256 to Rossing, PCT Publication WO 06/012033 to Rossing, PCT Publication WO 06/012050 to Rossing, PCT Publication WO 06/032902 to Caro et al., PCT Publication WO 06/041664 to Kieval, PCT Publication WO 06/125163 to Hagen, PCT Publication WO 07/013065 to Gross, PCT Publication WO 07/047152 to Rossing, PCT Publication WO 07/080595 to Levi, PCT Publication WO 07/114860 to Rossing, PCT Publication WO 07/118090 to Rossing, PCT Publication WO 07/136850 to Rossing, PCT Publication WO 07/136851 to Rossing, PCT Publication WO 08/039982 to Kieval, PCT Publication WO 08/083120 to Hagen, PCT Publication WO 08/083235 to Cates, U.S. Patent Application Publication 2003/0060858 to Kieval et al., U.S. Patent Application Publication 2003/0199806 to Kieval, U.S. Patent Application Publication 2004/0010303 to Bolea, U.S. Patent Application Publication 2004/0019364 to Kieval, U.S. Patent Application Publication 2004/0106976 to Bailey et al., U.S. Patent Application Publication 2004/0193092 to Deal, U.S. Patent Application Publication 2004/0254616 to Rossing, U.S. Patent Application Publication 2005/0027346 to Arkusz et al., U.S. Patent Application Publication 2005/0033407 to Weber et al., U.S. Patent Application Publication 2005/0096710 to Kieval, U.S. Patent Application Publication 2005/0154418 to Kieval et al., U.S. Patent Application Publication 2005/0203610 to Tzeng, U.S. Patent Application Publication 2005/0232965 to Falotico, U.S. Patent Application Publication 2005/0251212 to Kieval, U.S. Patent Application Publication 2005/0261257 to Vermeer, U.S. Patent Application Publication 2006/0004417 to Rossing, U.S. Patent Application Publication 2006/0004420 to Rossing, U.S. Patent Application Publication 2006/0004430 to Rossing, U.S. Patent Application Publication 2006/0074453 to Kieval et al., U.S. Patent Application Publication 2006/0111626 to Rossing, U.S. Patent Application Publication 2006/0265038 to Hagen, U.S. Patent Application Publication 2006/0293712 to Kieval, U.S. Patent Application Publication 2007/0021790 to Kieval, U.S. Patent Application Publication 2007/0021792 to Kieval, U.S. Patent Application Publication 2007/0021794 to Kieval, U.S. Patent Application Publication 2007/0021796 to Kieval, U.S. Patent Application Publication 2007/0021797 to Kieval, U.S. Patent Application Publication 2007/0021798 to Kieval, U.S. Patent Application Publication 2007/0021799 to Kieval, U.S. Patent Application Publication 2007/0038255 to Kieval, U.S. Patent Application Publication 2007/0038259 to Kieval, U.S. Patent Application Publication 2007/0038260 to Kieval, U.S. Patent Application Publication 2007/0038261 to Kieval, U.S. Patent Application Publication 2007/0038262 to Kieval, U.S. Patent Application Publication 2007/0049989 to Rossing, U.S. Patent Application Publication 2007/0060972 to Kieval, U.S. Patent Application Publication 2007/0106340 to Bolea, U.S. Patent Application Publication 2007/0156198 to Rossing, U.S. Patent Application Publication 2007/0156201 to Rossing, U.S. Patent Application Publication 2007/0167984 to Kieval, U.S. Patent Application Publication 2007/0185542 to Bolea, U.S. Patent Application Publication 2007/0185543 to Rossing, U.S. Patent Application Publication 2007/0276442 to Hagen, U.S. Patent Application Publication 2007/0276459 to Rossing, U.S. Patent Application Publication 2007/0282385 to Rossing, U.S. Patent Application Publication 2008/0004673 to Rossing, U.S. Patent Application Publication 2008/0009916 to Rossing, U.S. Patent Application Publication 2008/0009917 to Rossing, U.S. Patent Application Publication 2008/0046054 to Hjelle, U.S. Patent Application Publication 2008/0051767 to Rossing, U.S. Patent Application Publication 2008/0082137 to Kieval, U.S. Patent Application Publication 2008/0097540 to Bolea, U.S. Patent Application Publication 2008/01401671 to Hagen, U.S. Patent Application Publication 2008/0154349 to Rossing, U.S. Patent Application Publication 2008/0161865 to Hagen, U.S. Patent Application Publication 2008/0161887 to Hagen,
U.S. Patent Application Publication 2008/0167690 to Cody,
U.S. Patent Application Publication 2008/0167693 to Kieval,
U.S. Patent Application Publication 2008/0167694 to Bolea,
U.S. Patent Application Publication 2008/0167696 to Cates,
U.S. Patent Application Publication 2008/0167699 to Kieval,
U.S. Patent Application Publication 2008/0171923 to Bolea,
U.S. Patent Application Publication 2008/0172101 to Bolea,
U.S. Patent Application Publication 2008/0172104 to Kieval,
U.S. Pat. No. 3,650,277 to Sjostrand et al., U.S. Pat. No. 4,201,219 to Bozal Gonzalez, U.S. Pat. No. 4,791,931 to Slate, U.S. Pat. No. 4,938,766 to Jarvik, U.S. Pat. No. 6,442,424 to Ben-Haim, U.S. Pat. No. 6,375,666 to Mische, U.S. Pat. No. 6,522,926 to Kieval et al., U.S. Pat. No. 6,575,994 to Marin et al., U.S. Pat. No. 6,616,624 to Kieval, U.S. Pat. No. 6,669,686 to Singh, U.S. Pat. No. 6,764,498 to Mische, U.S. Pat. No. 6,850,801 to Kieval, U.S. Pat. No. 6,985,774 to Kieval, U.S. Pat. No. 7,044,981 to Liu et al., U.S. Pat. No. 7,158,832 to Kieval, U.S. Pat. No. 7,300,449 to Mische, U.S. Pat. No. 7,389,149 to Rossing, U.S. Pat. No. 7,395,119 B2 to Hagen "Ascorbic Acid Selectively Improves Large Elastic Artery Compliance in Postmenopausal Women," Moreau K. L., Hypertension 2005;45:1107

"Carotid sinus nerve blockade to reduce blood pressure instability following carotid endarterectomy: a systematic review and meta-analysis," Tang T. Y., Eur J Vasc Endovasc Surg. 2007 September;34(3):304-11

"Coronary artery baroreceptor-mediated changes in arterial pressure: a pilot study in conscious and anaesthetized sheep," Bennetts J. S., Clin Exp Pharmacol Physiol. 2001 September;28(9):768-72

"Effect of increased renal venous pressure on renal function," Doty J. M., The Journal of Trauma: Injury, Infection, and Critical Care: December 1999, Volume 47, Issue 6, p 1000.

"Glomerular ultrafiltration dynamics during increased renal venous pressure," J. R. Dilley, AJP—Renal Physiology, Vol 244, Issue 6 650-F658.

"Implantable penile venous compression device: initial experience in the acute canine model," Paick J., The Journal of Urology 1992, Vol. 148, No. 1, pp. 188-191

"On the excitation mechanism of the carotid baroceptors," Landgren S., Acta Physiol Scand. 1952 July 17;26(1):1-34

"The effects of altering mean pressure, pulse pressure and pulse frequency on the impulse activity in baroreceptor fibres from the aortic arch and right subclavian artery in the rabbit," Angell James J E, J Physiol. 1971 April;214(1):65-88

"Theoretical and electrophysiological evidence for axial loading about aortic baroreceptor nerve terminals in rats," Feng B, Am J Physiol Heart Circ Physiol. 2007 December; 293(6):H3659-72

SUMMARY OF THE INVENTION

For some applications, a subject's hypertension is reduced by modulating the subject's baroreceptor activity. Mechanical and other forces are applied directly or indirectly to one or more of the subject's blood vessels in order to modulate the baroreceptor response to the blood pressure. The forces are typically applied to arteries that are rich in baroreceptors, for example, the carotid arteries, the aorta, the subclavian arteries and/or arteries of the brain. For some applications, the forces are applied to other regions of the body that contain baroreceptors, such as the atria.

In accordance with respective applications, pressure, pull, stretch, torque and/or vibrational forces are applied. In accordance with respective applications, forces are applied directly and/or indirectly to a baroreceptor rich artery, upstream and/or downstream of a baroreceptor zone of a baroreceptor rich artery, and/or to a different artery that branches to or from a baroreceptor rich artery.

For some applications, forces are applied that directly affect the baroreceptors. Alternatively or additionally, forces are applied that cause changes in the shape of the artery, thus changing the wall tension of the artery. For example, the shape of the artery may be changed so as to cause changes in the geometry of the artery (e.g., from circular to elliptical) and/or to cause local changes in the shape of the artery (e.g., focal points of depression or curving in the arterial wall).

For some applications, forces are applied so as to change the dynamic behavior of an artery during the subject's cardiac cycle. For example, forces may be applied that cause accelerated systolic expansion, accelerated diastolic contraction, and/or other changes to the dynamic behavior of the artery. Alternatively or additionally, forces are applied that cause the artery to adopt a shape in which the artery has expanded and compressed regions. For example, forces may be applied that cause the assumption of a cog-wheel shape by the artery during portions of the cardiac cycle.

For some applications, a selective circumferential pressure applicator is coupled to an arterial wall at a longitudinal site of the artery. The pressure applicator is "selective" in that it applies pressure to the outer wall of the artery at two or more non-contiguous regions, at the longitudinal site, thus altering the response of the artery to pressure changes, and not at other regions at the longitudinal site that are between the two or more non-contiguous regions. For some applications, the pressure applicator applies pressure such that at the longitudinal site, between the non-contiguous regions, (a) there is at least one region of the artery that is more relaxed than in the absence of the device, and (b) there is at least one region of the artery that is more tense than in the absence of the device. For example, a pressure applicator (e.g., a clip) having an omega-shape, a U-shape, a V-shape, or a different shape is placed on the wall at a given longitudinal site of the artery. For some applications, the pressure applicator defines at least two surfaces, which are generally in opposition with each other (e.g., at an angle of less than 20 degrees, or less than 10 degrees from each other).

For some applications, a region of an arterial wall is expanded (e.g., radially expanded, or longitudinally stretched). While the wall is expanded, a device is attached to the wall, in order to inhibit contraction of the arterial wall. For some applications, an extravascular ring shaped device is placed on the outside of an artery, while the arterial wall is in the expanded state. The device has elastic properties that are such that when the device is on the arterial wall, the arterial wall undergoes a more compliant response to pressure changes than the arterial wall undergoes in the absence of the device, i.e., for a given change in pressure (e.g., from systole to diastole), the wall undergoes a greater change in shape than it would undergo in the absence of the device. This phenomenon is referred to herein as an increase in the effective compliance of the artery.

Although embodiments are described herein according to which one or more devices are placed around the outside of a subject's blood vessel, the scope of the present invention includes placing a device, as described herein, inside a subject's blood vessel. For example, a biodegradable device may be placed inside a subject's blood vessel, in order to apply a temporary treatment to the subject, before the device biodegrades. Alternatively, a non-biodegradable device is placed inside a subject's blood vessel for long-term treatment of the subject.

Although embodiments are described herein according to which one or more devices are placed around, or within, a subject's artery, the scope of the present invention includes placing a device as described herein inside or outside any tubular organ of the subject, for example a tubular organ of the subject's gastrointestinal tract, or a vein of the subject.

There is therefore provided, in accordance with some applications of the present invention, apparatus for reducing hypertension of a subject, including:

a selective circumferential pressure applicator, including:
at least two surfaces that are configured to increase baroreceptor activity of the subject, by applying pressure to an artery of the subject at two or more respective non-contiguous regions around a circumference of the artery, at a longitudinal site of the artery, such that between the non-contiguous regions, at the longitudinal site:
there is at least one region of the artery that is more relaxed than in the absence of the device, and
there is at least one region of the artery that is more tense than in the absence of the device; and
a joint configured:
to couple the surfaces to each other, and
for at least a portion of a cardiac cycle of the subject, not to contact the artery of the subject.

For some applications, the joint is a rigid joint.

For some applications, the joint is a flexible joint.

For some applications, the surfaces are configured to apply the pressure to the artery such that the region of the artery that is more tense is between the joint and the region of the artery that is more relaxed.

For some applications, the surfaces are configured to apply the pressure to the artery such that the region of the artery that is more relaxed is between the joint and the region of the artery that is more tense.

For some applications, the at least two surfaces are slidably coupled to each other.

For some applications, the surfaces are oriented in general opposition with respect to each other.

For some applications, an angle between the two surfaces is less than 20 degrees.

For some applications, the angle between the two surfaces is less than 10 degrees.

There is additionally provided, in accordance with some applications of the present invention, a method for reducing hypertension of a subject, including:

using at least two surfaces that are coupled to each other by a joint, applying pressure to an artery of the subject at two or more respective non-contiguous regions around a circumference of the artery, at a longitudinal site of the artery, such that between the non-contiguous regions, at the longitudinal site:
there is at least one region of the artery that is more relaxed than in the absence of the device, and
there is at least one region of the artery that is more tense than in the absence of the device, by
placing the joint such that for at least a portion of a cardiac cycle of the subject the joint does not contact the artery of the subject.

For some applications, applying the pressure to the artery includes applying pressure to the artery at a region of the artery that is rich in baroreceptors.

For some applications, applying the pressure to the artery includes applying pressure to the artery at a location selected from the group consisting of an upstream location, and a downstream location from a region of the artery that is rich in baroreceptors.

For some applications, the method further includes selecting a location as the selected location such that at least a portion of a pressure change induced in the artery at the location, by the surfaces, reaches the region of the artery that is rich in baroreceptors after a time delay from when the pressure change was induced at the location, the time delay being such that baroreceptor stimulation at the region of the artery that is rich in baroreceptors, as a result of the portion of the pressure change that reaches the region of the artery that is rich in baroreceptors, is greater than if the pressure change was induced by the surfaces at the region of the artery that is rich in baroreceptors.

There is additionally provided, in accordance with some applications of the present invention, apparatus, including:

a pressure-applying element configured to be coupled to a first blood vessel of a subject;
a pressure-receiving element configured to automatically undergo a shape change due to pressure exerted thereon by a portion of the subject's body that is not the first blood vessel; and
a pressure-conveying element, configured to convey fluid pressure from the pressure-receiving element to the pressure-applying element, in response to the shape change of the pressure-receiving element.

For some applications, the pressure-receiving element includes a chamber configured to be placed in a pleural cavity of the subject and to undergo changes in shape due to pressure exerted thereon by tissue in the subject's pleural cavity.

For some applications, the pressure-conveying element includes a regulator configured to cause negative pressure to be applied to the first blood vessel, in response to positive pressure being exerted on the pressure-conveying element by the pressure-receiving element.

For some applications, the pressure-receiving element and the pressure-applying element respectively include first and second portions of a scissor-action device.

For some applications, the pressure-applying element includes a cuff configured to be placed at least partially around the circumference of the first blood vessel.

For some applications, the pressure-receiving element includes a cuff configured to be placed at least partially around the circumference of a second blood vessel of the subject.

There is further provided, in accordance with some applications of the present invention, a method, including:

automatically applying pressure to a first blood vessel of a subject, using pressure generated at a portion of a body of the subject that is not the first blood vessel, by:
coupling a pressure-applying element to the first blood vessel; and
coupling a pressure-receiving element to the portion of the subject's body,
the pressure-receiving element being configured to automatically undergo a shape change due to pressure exerted thereon by the portion of the subject's body, and
the pressure-applying element being in fluid communication with the pressure-receiving element, via a pressure-conveying element that is configured to convey fluid pressure from the pressure-receiving element to the pressure-applying element, in response to the shape change of the pressure-receiving element.

There is further provided, in accordance with some applications of the present invention, a method, including:

expanding an artery of a subject to an expanded state; and inhibiting contraction of the artery, by coupling an element to the artery, while the artery is in the expanded state thereof.

For some applications, expanding the artery includes relaxing the artery by administering a substance to the subject.

For some applications, expanding the artery includes applying negative pressure to an outer wall of the artery.

For some applications, expanding the artery includes injecting fluid into the artery.

For some applications, expanding the artery includes inflating a balloon inside the artery.

For some applications:

expanding the artery includes longitudinally stretching the artery, and inhibiting contraction of the artery includes, while the artery is stretched, coupling a first element to the artery at a first position along the length of the artery and coupling a second element to the artery at a second position along the length of the artery, the first and second elements being separated from each other by a third element, which prevents the first and second elements from being less than a fixed minimum distance from each other.

For some applications, expanding the artery includes radially expanding the artery.

For some applications, coupling the element to the artery includes coupling a ring to the artery.

For some applications, coupling the element to the artery includes coupling first and second surfaces to the artery, the first and second surfaces being coupled to each other at a fixed minimum distance from each other.

For some applications, inhibiting contraction of the artery includes increasing an effective compliance of the artery relative to compliance of the artery in the absence of the device.

For some applications, increasing the effective compliance of the artery includes increasing baroreceptor stimulation at the artery relative to baroreceptor stimulation at the artery in the absence of the device.

There is additionally provided, in accordance with some applications of the present invention, a method, including:

identifying a subject suffering from a condition selected from the group consisting of hypertension and hypotension;

determining a relationship between (a) a variable that is indicative of baroreceptor stimulation of the subject, and (b) blood pressure in an artery of the subject;

subsequent to determining the relationship, implanting a device inside a body of the subject;

while the device is implanted, determining the relationship between (a) the variable that is indicative of baroreceptor stimulation of the subject, and (b) blood pressure in the artery of the subject; and determining that the subject's condition has been treated at least in part, by determining that, in response to the implantation of the device, the relationship between (a) the variable that is indicative of baroreceptor stimulation of the subject, and (b) the blood pressure in the artery has changed.

For some applications, the method further includes:

determining the relationship between (a) the variable that is indicative of baroreceptor stimulation of the subject, and (b) blood pressure in an artery of the subject, when the device is placed at a plurality of implantation sites inside the subject's body; and in response to determining the relationship when the device is placed at the plurality of sites, selecting an implantation site for the device.

For some applications, determining that the relationship has changed includes determining that, in response to the coupling of the device to the subject's artery, a relationship between (a) an R-R interval of an ECG signal of the subject, and (b) blood pressure in the subject's artery has changed.

There is further provided, in accordance with some applications of the present invention, a method, including:

identifying a subject as suffering from a medical condition;

in response to the identifying, irreversibly changing a shape of an arterial wall of the subject, by inducing a pressure change of the arterial wall, by coupling a device to the arterial wall; and causing the pressure change induced by the device to be discontinued after coupling the device to the arterial wall.

For some applications, causing the pressure change to be discontinued includes intermittently deactivating and reactivating the device to cause the pressure change.

For some applications, causing the pressure change to be discontinued includes explanting the device.

For some applications, causing the pressure change to be discontinued includes selecting as the device that is coupled to the arterial wall, a device that is biodegradable.

For some applications, causing the pressure change to be discontinued includes coupling the device to the arterial wall via a coupling element that is biodegradable.

For some applications, causing the pressure change to be discontinued includes withdrawing fluid from the device via a self-sealing reservoir inside a body of the subject.

For some applications, causing the pressure change to be discontinued includes deflating an inflatable element via which inflation element the device is coupled to the arterial wall.

For some applications, causing the pressure change to be discontinued includes inflating an inflatable element such that two or more force-providing portions of the device are separated from each other.

For some applications, irreversibly changing the shape of the arterial wall includes increasing baroreceptor sensitivity of the arterial wall.

For some applications, causing the pressure change to be discontinued includes selecting as the device that is coupled to the arterial wall, a device that stops applying pressure to the artery due to the shape of the artery having changed.

There is additionally provided, in accordance with some applications of the present invention, a method, including:

identifying a subject as suffering from a condition selected from the group consisting of hypertension and hypotension; and in response to the identifying, irreversibly altering compliance of an artery of the subject in a vicinity of baroreceptors, by performing an action selected from the group consisting of:

coupling a device to the artery for at least 2 days and subsequently removing the device;

treating the artery itself, regardless of any presence of plaque on the artery; and locally, applying a chemical to the artery in the vicinity.

For some applications, performing the selected action includes locally, applying the chemical to the artery in the vicinity.

For some applications, performing the selected action includes treating the artery itself, regardless of any presence of plaque on the artery.

For some applications, performing the selected action includes coupling a device to the artery for at least 2 days and subsequently removing the device.

For some applications, coupling the device to the artery includes inserting the device inside the artery.

There is further provided, in accordance with some applications of the present invention, a method, including:

identifying a subject suffering from hypertension; and in response to the identifying, coupling to the outside of the subject's artery an element that prevents expansion of the artery to a systolic diameter of the artery that would occur in the absence of the implanted device, but applies substantially no compressive force to the artery during diastole of the subject.

For some applications, coupling the element to the outside of the subject's artery includes coupling to the outside of the subject's artery an element having an internal dimension that is between diastolic and systolic diameters of the artery.

There is further provided, in accordance with some applications of the present invention, a method, including:

identifying a region of an arterial wall of a subject that is rich in baroreceptors by:

applying suction to an outer wall of the artery at the region; and determining that baroreceptor sensitivity of the subject has increased in response to applying the suction to the region.

For some applications, applying the suction includes:

placing a surface on the outer wall of the artery at the region; and bringing the outer wall of the artery into contact with the surface at the region by applying the suction, and the method further includes, subsequent to identifying the region as being rich in baroreceptors:

placing the surface on the outer wall of the artery at the region;

bringing the outer wall of the artery into contact with the surface at the region by applying the suction; and suturing a device to the region, by passing a suture through a hole in the surface, while the outer wall of the artery is in contact with the surface.

There is additionally provided, in accordance with some applications of the present invention, apparatus for reducing hypertension of a subject, including:

a ring configured to be coupled to an artery of the subject, the ring including a non-bulging portion thereof, and a bulging portion thereof, the ring configured such that:

during diastole of the subject, the bulging portion does not exert more pressure on the artery than the non-bulging portion; and during systole of the subject, the bulging portion exerts more pressure on the artery than the non-bulging portion.

The present invention will be more fully understood from the following detailed description of embodiments thereof, taken together with the drawings, in which:

BRIEF DESCRIPTION OF THE DRAWINGS

FIG. 2A is a schematic illustration of an elliptical device placed on an artery, in accordance with some applications of the present invention;

FIG. 2B is a schematic illustration of a double ringed elliptical device placed on an artery, in accordance with some applications of the present invention;

FIG. 3A is a schematic illustration of an artery with an omega-shaped clip attached to the artery, in accordance with some applications of the present invention;

FIGS. 3B-C are schematic cross-sectional illustrations of the omega-shaped clip on the artery, during diastole and during systole respectively, in accordance with some applications of the present invention;

FIGS. 6A-B are schematic illustrations of respective longitudinal stretch devices placed on an artery, in accordance with some applications of the present invention;

FIGS. 7A-B are schematic illustrations of a passive compression ring placed around an artery, respectively during diastole and during systole, in accordance with some applications of the present invention;

DETAILED DESCRIPTION OF THE EMBODIMENTS

Figure 1A:
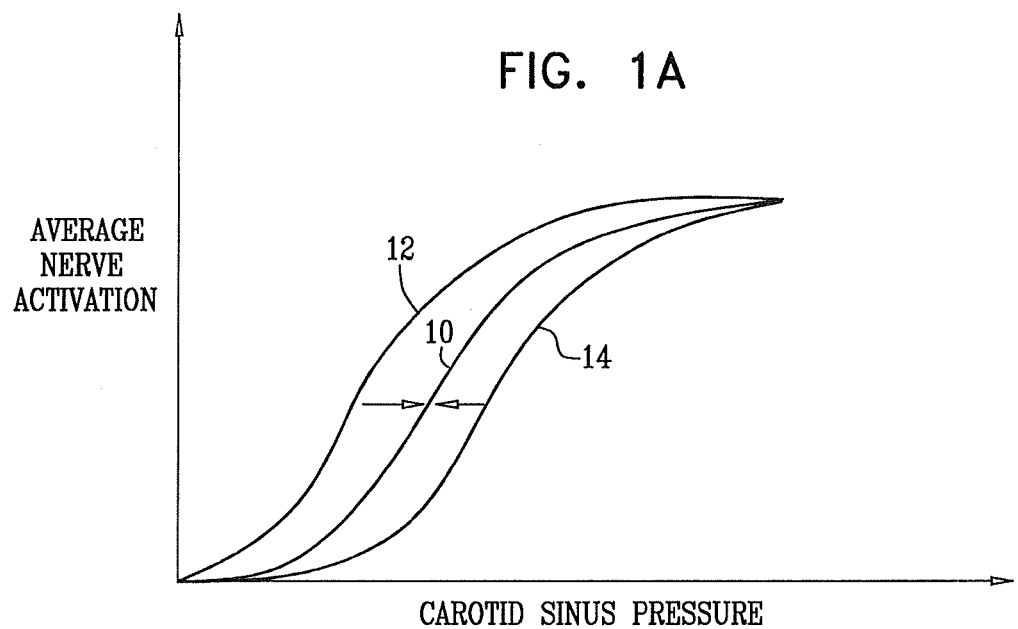
FIG. 1A is a graph of average nerve activation (as a percentage of the maximum nerve activation) against carotid sinus pressure for normotensive, hypertensive and hypotensive subjects.
Figure 1B:
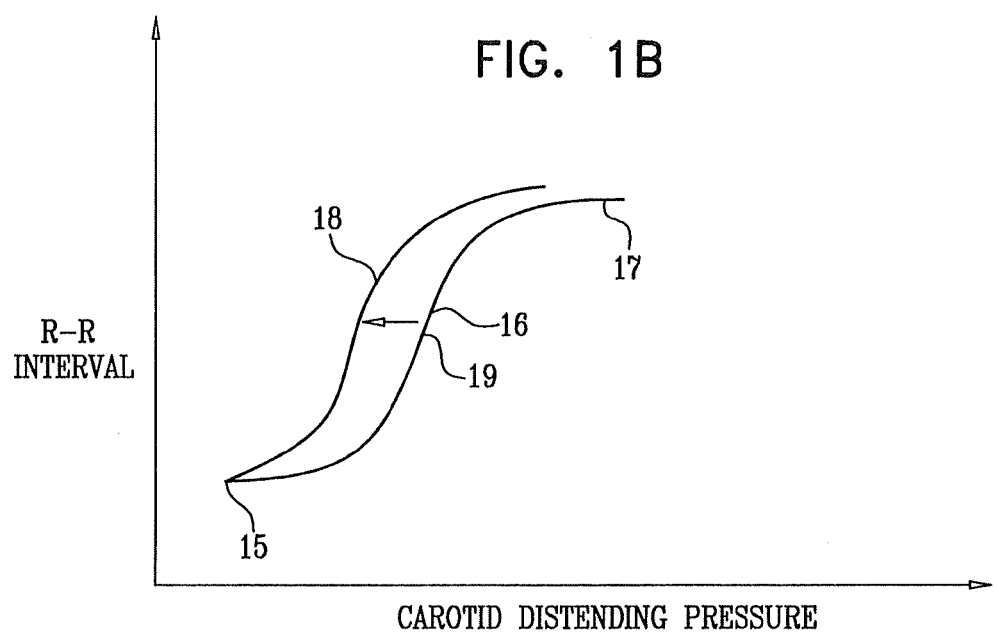
FIG. 1B is a graph of the R-R interval of normotensive and hypertensive subjects' ECG cycles as a function of carotid distending pressure.

Reference is now made to FIGS. 1A-B. FIG. 1A is a graph of average nerve activity (as a percentage of the maximum nerve activity) against carotid sinus pressure for normotensive (curve 10), hypotensive (curve 12), and hypertensive (curve 14) subjects. FIG. 1B is a graph of the R-R interval of normotensive (curve 18) and hypertensive (curve 16) subjects' ECG cycles against the carotid distending pressure of the subjects.

Baroreceptor pressure-activity relationship may be described by a curve relating carotid distending pressure to baroreceptor activity, as shown in FIG. 1A. For hypertensive subjects this curve is shifted to the right relative to that of normotensive subjects, as shown. This is because in hypertensive subjects, there is less baroreceptor activity at any given distending pressure. In response to the low baroreceptor activity, the subject's blood pressure is increased, resulting in hypertension. For hypotensive subjects the curve is shifted to the left relative to that of normotensive subjects, as shown. For some applications, the curve of a hypertensive subject is shifted to the left, by increasing baroreceptor activity at all distending pressures, as indicated by left-pointing arrow in FIG. 1A. Alternatively, the curve of a hypotensive subject is shifted to the right, by decreasing baroreceptor activity at all distending pressures, as indicated by right-pointing arrow in FIG. 1A.

An indication of a subject's baroreceptor pressure-activity relationship (i.e., the relationship between changes in blood pressure and the resultant changes in baroreceptor activity) may further be determined by plotting the subject's carotid distending pressure against the subject's R-R interval, as shown in FIG. 1B. In a normal subject, in response to higher carotid distending pressure, there is increased baroreceptor activity. In response to the increased activity, the length of the subject's cardiac cycle is increased (i.e., the subject's heart rate decreases), resulting in a lengthened R-R interval. The curve shown in FIG. 1B is a sigmoid curve that has several points on it, e.g., threshold point 15, saturation point 17 and centering point 19. The threshold point is the point where additional reductions in pressure do not cause further shortening of the R-R interval. The saturation point is the point at which additional increases in pressure do not cause further lengthening of the R-R interval. The centering point is a point on the curve at which positive and negative pressure changes cause equal and opposite changes in the R-R interval.

For some applications, there is facilitated a sustained and controllable change in the baroreceptor pressure-activity relationship such that the curve will shift to the left, as indicated by the arrow in FIG. 1B. A treatment is applied, such that at any given distending pressure, a subject's baroreceptor activity is increased. As a result, the subject's heart rate is decreased, and the R-R interval is lengthened.

For some applications (not shown), the techniques of the present invention are applied to a subject in order to shift to the right the curve of the subject's carotid distending pressure against the subject's R-R interval. Some subjects have an actual blood pressure that exceeds the saturation point of the subjects' baroreceptors, therefore the baroreceptors are unable to respond to acute blood pressure changes of the subject. For such subjects, shifting the curve to the right restores or improves the ability of the baroreceptors to respond to changes in blood pressure. The inventors hypothesize that restoring the ability to respond to changes in blood pressure to a subject's baroreceptors is beneficial to the subject, regardless of the absolute blood pressure values of the subject. For example, restoring the response of baroreceptors to acute blood pressure changes may have an effect on the adaptive capabilities of the central nervous system.

For some applications, techniques as described herein are applied to a subject in order to shift upwards or downwards the curve of the subject's carotid distending pressure against the subject's R-R interval. That is, the level of baroreceptor activity at the threshold, saturation and centering points is increased or decreased without affecting the blood pressures at which respective points are reached. By contrast, if the curve is shifted to the left, then, for example, the centering point is reached at a lower carotid distending pressure.

Typically, one or more devices described herein are implanted on the outside of one or more baroreceptor-rich arteries, and/or other arteries or veins of a subject, for treating hypertension of the subject. The devices apply mechanical and/or other forces to the one or more arteries in order to modulate the baroreceptor response to the blood pressure. Forces are applied to increase wall tension, reduce wall tension, and/or to increase or decrease changes in wall tension over the course of the subject's cardiac cycle.

For some applications, one or more of the devices described herein are implanted on one or both sides of, or around, the subject's carotid artery. For example, the devices may be implanted on the common carotid artery, the internal carotid artery or the external carotid artery, or at the carotid bifurcation. Alternatively or additionally, the one or more devices are implanted outside the subject's aorta, for example, around the aortic arch or the thoracic descending aorta. For some applications, one or more of the devices are implanted outside the subject's renal arteries, in order to modulate the effective pressures sensed by pressure-sensitive cells of the subject's kidney.

Typically, one or more devices are implanted in a vicinity of a baroreceptor-rich area of an artery. For some applications, the devices are implanted upstream or downstream of the location of baroreceptors. When located upstream or downstream, changes in arterial wall tension and internal pressure, caused by the devices, are conveyed to the baroreceptor with a certain delay (determined by the wave traveling velocity of the pressure pulse and the distance from the device to the baroreceptors). For some applications, the devices are located such that the delay amplifies the curves and slopes of the pressure changes at the baroreceptor site, thus increasing baroreceptor sensitivity.

For some applications, baroreceptors are affected by inducing changes in the dynamics of the blood flow. For example, effective arterial wall pressure may be increased by induction of turbulent blood flow within the artery. In accordance with respective applications, such turbulence is induced by causing changes in the shape of the blood vessel, by causing local irregularities in the blood vessel wall, and or by applying external forces that force the blood flow into turbulence (e.g., by applying vibration, pulsation, etc.). For some applications, baroreceptors are stimulated by applying pressure to the blood vessel, without reducing blood flow through the blood vessel.

For some applications, any of the devices described herein is attached to an artery, in accordance with one or more of the following techniques:

(a) The device is attached to the artery while the artery is in an expanded state. The device is attached such that the device maintains the artery in the expanded state. For some applications, the device is attached to the artery such that the effective compliance of the artery is increased by having expanded the artery radially. This typically causes increased baroreceptor stimulation in the artery, by increasing the change in shape that the artery undergoes during the cardiac cycle. Alternatively or additionally, the device causes stretching of the baroreceptors by being attached such that the artery is longitudinally stretched.

(b) The device is attached to the artery such that the artery is compressed for at least a portion of the cardiac cycle, relative to when the device is not attached to the artery. Typically, this increases transmural tension in the arterial wall, thereby stimulating baroreceptors.

(c) The device is attached to the artery at a longitudinal site of the artery, such that pressure is applied to the arterial wall at non-contiguous local pressure points around the circumference of the arterial wall. Typically, local pressure points are selected that are identified as being rich in baroreceptors.

(d) For some applications (e.g., when applied to an artery post-surgery), the device uniformly limits expansion of the artery (e.g., during systole), thereby reducing tension in the arterial wall.

For some applications, the implanted device is stiff and sized to have an internal diameter that is between the systolic external diameter of the artery in the absence of the device and the diastolic external diameter of the artery in the absence of the device. The device is placed around the artery such that when the artery expands during systole, the artery is squeezed against the stiff internal surface of the device, causing an increase in local pressure. In accordance with respective applications, the internal surface of the device is smooth, or has irregularities, such as local protrusions. The local protrusions cause focal irregularities in the arterial wall, with corresponding areas of increased wall tension at or near the irregularities.

For some applications, one or more of the devices described herein is implanted around a subject's artery to increase the wall tension of the artery, to induce release of nitric oxide and/or other endothelial derived factors, to induce vascular growth, to inhibit atherosclerosis, and/or to prevent restenosis. For example, one or more of the devices described herein may be implanted around an artery supplying blood to the leg (such as the superficial femoral artery), to treat peripheral vascular disease of the leg by inducing arterial relaxation and neovascularization via induction of endothelial release of nitric oxide and/or vascular endothelial growth factor. Alternatively or additionally, one or more of the devices described herein may be implanted around a subject's internal pudendal artery to treat impotence, around a facial artery to rejuvenate the skin, and/or around a vein implanted as a graft or that is going to be grafted, to maintain graft potency over time.

For some applications, a blood vessel is stretched longitudinally. For some applications, the longitudinal stretching of the blood vessel is facilitated by limiting blood flow through the blood vessel. For example, blood flow may be stopped completely (e.g., by clipping a distal portion of the blood vessel), or reduced (e.g., by reducing blood flow through the blood vessel by at least 50%). The blood pressure in the artery pressurizes the occluded, or partially occluded region of the artery, causing the artery to become longitudinally stretched. For some applications, the blood flow through an artery is completely stopped by occluding a distal portion of the artery, and, in addition, a longitudinal force is applied to the proximal end of the artery. Alternatively or additionally, the flow through the blood vessel is stopped or reduced, as described, for only a portion of the cardiac cycle, thus causing the extent of the stretching of the blood vessel to vary in coordination with the cardiac cycle.

For some applications, blood flow through an artery that contains baroreceptors is reduced, and, in addition, longitudinal forces are applied to a baroreceptor-rich area of the artery. For some applications, blood flow is reduced through a given branch of the common carotid artery in order to stimulate baroreceptors of the given branch. Typically, blood flow is reduced through a branch of the common carotid artery other than the internal carotid artery, e.g., the external carotid artery. For some applications, a minor branch of the common carotid artery is occluded in order to stimulate baroreceptors that are located at the carotid sinus. For example, occluding the minor branch stimulates the carotid sinus baroreceptors by causing turbulent flow at the carotid sinus, or in accordance with other techniques described herein.

For some applications, a device is attached to an artery when the artery is artificially relaxed by a smooth muscle relaxant, such as acetylcholine, or papaverine. Alternatively, the device is attached to the artery when the artery is forcefully expanded to an increased diameter, by increasing the internal pressure in the artery (for example, using fluid injection or a balloon) or by applying an external negative pressure to the artery. Typically, if the device is connected to the artery while the artery is artificially expanded, the device will later apply an outward pulling force on the artery when the artery attempts to contract back to natural size.

For some applications, devices are attached to arteries in accordance with techniques described herein, for reasons other than to stimulate baroreceptors. For example, the techniques described herein may be used for attaching a device to a renal artery, in order to increase renal perfusion.

Reference is now made to FIG. 2A, which is a schematic illustration of an elliptical device 30 implanted on an artery 20, in accordance with some applications of the invention. The device is typically composed of plastic or metal. For example, the device may be composed of a shape memory alloy such as nitinol. For some applications, device 30 is elastic and adopts a circular shape if radial forces are applied to its center, but has a tendency to adopt an elliptical shape in the absence of external forces.

Reference is now made to FIG. 2B, which is a schematic illustration of two or more elliptical devices 30 implanted on artery 20, the elliptical devices being connected by longitudinal rods 31, in accordance with some applications of the invention. For some applications, the rods are elastic. For some applications, the rods are formed as a single integrated unit with the two or more ellipses. Alternatively, the rods are formed separately from the ellipses. For some applications, using a device having two or more ellipses causes increased baroreceptor firing in a larger area of the artery, as compared to the device with the single ellipse shown in FIG. 2A.

For some applications, elliptical device 30 is made of two separate parts that are connected after they have been placed around the artery. FIG. 2A shows device 30 having two separate parts, which are coupled to each other around the artery at coupling regions 23. Alternatively, the device is originally in an open configuration and is folded into an ellipse around the artery, as shown in FIG. 2B. FIG. 2B shows each ellipse 30 having one coupling region 23, at which region the open edges each of the ellipses are coupled to each other, in order to close the ellipse.

Typically, placement of device 30 over the artery deforms the cross sectional shape of the artery into an ellipse while arterial pressure is low (e.g., during diastole). When blood pressure rises (e.g., during systole) the device is forced into a more circular shape.

For some applications, the transition between the elliptical and circular cross sectional shapes can cause stretching of the baroreceptors that is greater than would be in the absence of the device, the device thus causing increased baroreceptor stimulation. Alternatively or additionally, the device increases the rate at which the arterial wall stretches in response to pressure (i.e., the device artificially increases the effective compliance of the artery) in a manner that lowers the baroreceptor threshold and increases the firing rate of baroreceptors.

It has been observed that baroreceptors respond to the rate of change of pressure in a blood vessel as well as to the absolute pressure within the blood vessel. Evidence for this is seen, for example, in the fact that baroreceptor impulse frequency is higher during systole than during diastole, since the rate of change of pressure is greater during systole, for any given pressure. In addition, an increase in the rate of change of pressure (dP/dT) has been shown to lower the threshold pressures of carotid baroreceptor, as described in articles by Landgren (1952), and James Angell (1974), cited hereinabove, both of which articles are incorporated herein by reference. Therefore, increasing the rate at which the arterial wall responds to pressure (i.e., increasing effective compliance of the arterial wall) increases the response rate of baroreceptors to naturally-occurring changes in the subject's blood pressure.

Reference is now made to FIGS. 3A-C, which are schematic illustrations of an omega-shaped selective circumferential pressure applicator 60 implanted around artery 20, in accordance with some applications of the present invention. FIG. 3B is a cross-sectional view of pressure applicator 60 around the artery during diastole, and FIG. 3C is a cross-sectional view of pressure applicator 60 around the artery during systole. An omega-shaped pressure applicator (whose name is based on the letter Q) has two feet, and a central arched joint 63, which joins the two feet. (For some applications, the joint forms an integrated unit with the feet.) The pressure applicator includes two surfaces 61 of the feet. For some applications (not shown), the two surfaces are generally in opposition to each other (e.g., at an angle of less than 20 degrees, or less than 10 degrees from each other), and the squeezing force that the surfaces apply to the artery maintains the pressure applicator on the artery. Alternatively or additionally, the surfaces are sutured to the artery with sutures (as shown), and/or are attached to the artery by other means, as described herein. At the longitudinal implantation site of the device on the artery, respective surfaces of surfaces 61 apply pressure to non-contiguous regions around the circumference of the artery.

Typically, pressure applicator 60 is attached to the artery such that for at least a portion of the subject's cardiac cycle (and, typically, for the entire cardiac cycle) the artery does not contact joint 63. Further typically, the pressure applicator engages the artery such that there is a tense area 21 of the artery and a relaxed area 22 of the artery. Relaxed area 22 is shown on the side of the midline of the artery that is closer to joint 63 (i.e., between joint 63 and tense area 21), and tense area is shown on the side of the midline of the artery that is further from joint 63. However, for some applications, the pressure applicator is attached to the artery such that the area on the side of the midline of the artery that is further from joint 63 is relaxed and the area on the side of the midline of the artery that is closer to joint 63 is tense. For some applications, the relaxed and tense areas are caused by surfaces 61 of the pressure applicator not applying pressure along a midline A-A (shown in FIG. 3B) of the artery. Rather, the surfaces grip the artery on the side of midline A-A that is closer to joint 63 (in which case the relaxed area is on the side of the artery closer to the joint, as shown). Alternatively, the surfaces reach around the artery and grip the artery on the side of midline A-A that is further from joint 63 (in which case the relaxed area is on the side of the artery further from the joint, not as shown).

For some applications, pressure elevation from diastole to systole causes a change in the shape of the relaxed area of the artery that is greater than the change in shape would be in the absence of the pressure applicator (FIG. 3C). Alternatively or additionally, the omega-shaped pressure applicator causes increased baroreceptor signaling in tense area 21. Typically, this is because tense area 21 is stretched even during diastole. Therefore, during systole, tense area 21 becomes more stretched than area 21 would be in the absence of pressure applicator 60. The pressure applicator has an effect on the baroreceptor pressure-activity curve that is dependent on the proportions between the sizes of the relaxed and tense areas and the mechanical properties of the pressure applicator and artery.

For some applications, several pressure applicators are connected to each other (e.g., by a spine element) such that longitudinal movement of the pressure applicators with respect to the artery is reduced or prevented.

Figure 3D:
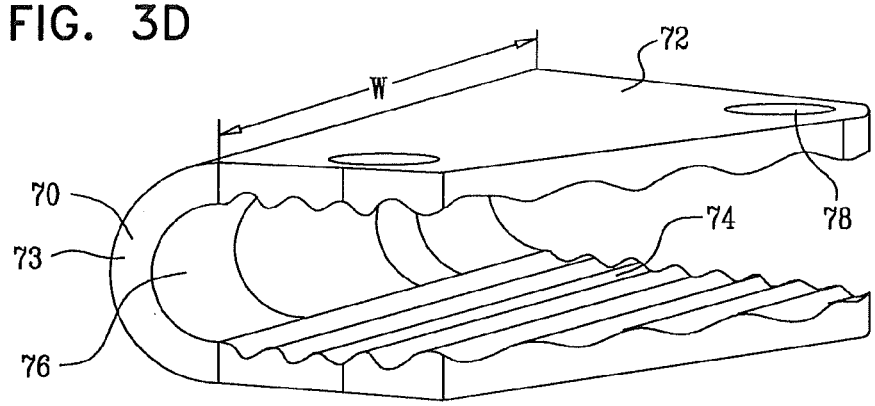
FIGS. 3D-F are schematic illustration of devices for compressing an artery, in accordance with some applications of the present invention.

Reference is now made to FIG. 3D, which is a schematic illustration of a U-shaped pressure applicator 70, e.g., a U-shaped clip, in accordance with some applications of the present invention. For some applications, a similar effect to that described with respect to omega-shaped pressure applicator 60 (described with reference to FIGS. 3A-C) is achieved with a pressure applicator that is U-shaped, as shown. Side branches 72 of the U-shaped clip are generally in opposition to each other, and are coupled to each other by a joint 73. For some applications the side branches and the joint form a single integrated unit. At the longitudinal implantation site of the device on the artery, respective side branches apply pressure to non-contiguous regions around the circumference of the artery. The side branches are attached to the artery, for example, by including a rough surface, and/or gripping elements (e.g., barbs) on the inner surface of the side branches. For some applications, ridges 74 that are generally parallel to the longitudinal axis of the artery are included on the inner surface of the side branches, as shown. Ridges 74, the rough inner surface of the side branches, and/or gripping elements prevent the clip from slipping off the artery. For some applications, arms 72 are rod-like, for example, having a width W of less than 5 mm. For some applications, the U-shaped clip is attached to an artery such that there is a small relaxed area of the artery at a region 76 inside joint 73 of the U-shaped clip, and a tense area of the artery outside the U of the U-shaped clip (i.e., between the arms, but not in the curved portion of the U), or vice versa. The relaxed and tense areas of the artery are generally similar to the relaxed and tense areas of the artery generated by placing omega-shaped pressure applicator 60 on the artery, as described with reference to FIGS. 3A-C.

As shown in FIG. 3D, clip 72 typically has an opening on one side, to facilitate placement of the clip on the artery without the need for lateral dissection of the artery. For some applications, the clip is designed to accommodate the narrowing carotid sinus. For example, the clip may have a shape that narrows across the width of the clip, as shown in FIG. 3D. For some applications, the clip is attached to the artery by suturing the clip to the artery via holes 78 of the clip. Alternatively, the clip is attached to the artery using other mechanisms, as described herein.

Figure 3E:
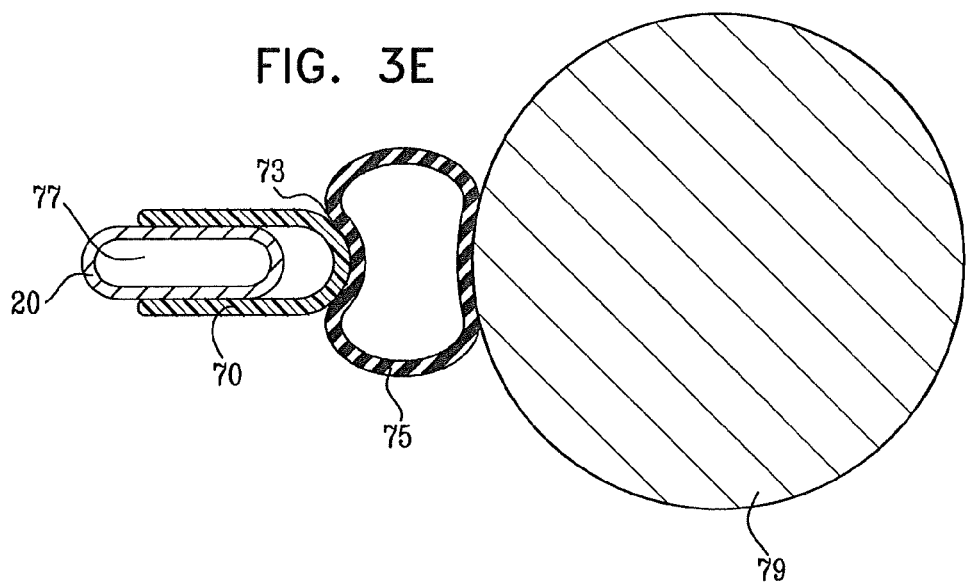

Reference is now made to FIG. 3E, which is a schematic illustration of U-shaped clip 70, in accordance with some applications of the present invention. For some applications, the clip is placed on the internal carotid sinus from the medial aspect of the carotid bifurcation, with the open side of the U facing towards the lateral aspect of the sinus. For some applications, the device further comprises a volume-occupying element 75 on the side of the U that is opposite to opening 77 of the clip, to press against tissue that is medial to the carotid bifurcation and to generate force on the device so as to maintain the carotid bifurcation within the U-shape of the device. For example, the trachea 79 and/or muscles adjacent to the trachea may provide resistance that pushes the volume—occupying element toward the clip, as shown. For some applications, as shown, the U of U-shaped clip 70 is deep enough to allow the carotid bifurcation to lie within the device without coming in contact with joint 73, for at least a portion of (and, typically, for all of) the subject's cardiac cycle.

For some applications, a clip is used that is generally U-shaped, in which one or both of the arms of the U is elastic. For such applications, the arms of the clip either apply inward force on the artery at all times, or only at times where the arms are pushed beyond the elastic resting point of the device.

For some applications, a V-shaped clip is used instead of a U-shaped clip. The V-shaped clip is generally similar to the U-shaped clip, except that side branches 72 of the clip are not parallel to each other, even when the clip is at rest. For some applications, the side branches of the V-shaped clip are generally in opposition to each other, but are not parallel to each other. For example, the side branches may be in general opposition to each other by being at an angle of less than 20 degrees, or less than 10 degrees from each other. Alternatively, the side branches of the V-shaped clip are not generally in opposition to each other. For example, the side branches may form a right angle with each other. Typically, when the side branches of the V-shaped clip are not generally in opposition to each other, the side branches are attached to the arterial wall using attachment techniques described herein (e.g., suture or glue).

Whether U- or V-shaped, clip 70 has a generally similar effect on baroreceptor firing as that described with respect to elliptical device 30, and/or pressure applicator 60. For some applications, clip 70 additionally causes local tension points on the wall of artery 20, which cause increased baroreceptor activity. For example, at non-contiguous regions of contact between side branches 72 of clip 70 and the artery, there is increased baroreceptor activity. Alternatively or additionally, at areas of the arterial wall that are made to be tense and/or relaxed by the clip, there is increased baroreceptor activity. For some applications, clip 70 increases the transmural pressure detected by the arterial wall, which is known to increase baroreceptor activity.

For some applications, clip 70 exerts an outward force on the arterial wall, which typically requires coupling of the spring to the wall. For example, clip 70 may be coupled to the arterial wall with sutures, biological glue, clips, and/or in accordance with other techniques described herein. For some applications, the clip becomes coupled to the artery due to fibrosis. For some applications, the clip is coupled to the arterial wall while the artery is in an expanded state, using the techniques described herein. For example, during implantation of clip 70 (or another of the devices described herein), the artery is actively radially stretched. While the artery is stretched, the clip is connected to the artery. Subsequently, the side branches of the clip are maintained a fixed minimum distance from each other. Thus, even when the artery is no longer being actively stretched, clip 70 maintains the artery in a radially stretched state.

Figure 3F:
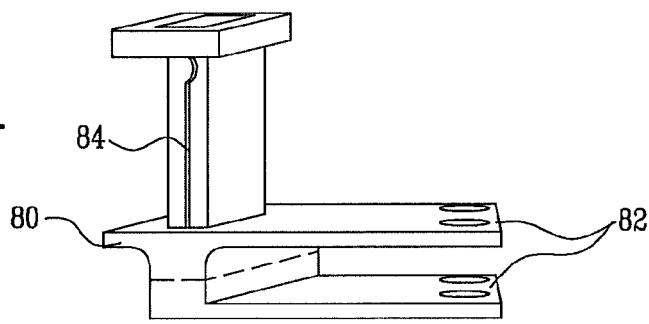

Reference is now made to FIG. 3F, which is a schematic illustration of a device 80 that includes two plates 82 that are slidably coupled to each other, and are for compressing an artery, in accordance with some applications of the present invention. The plates are generally in opposition to each other. For example, the plates may be parallel to each other, or may be at an angle of less than 20 degrees, or less than 10 degrees from each other. Device 80 includes an axis 84 that allows perpendicular motion of the two plates towards each other, thus allowing the device to move from open to closed positions, and vice versa, while maintaining the angular position of the plates with respect to each other. Typically, during implantation of the device, the device is placed around the artery while the device is in the open position. When the device is positioned at the longitudinal implantation site of the device on the artery, the plates are closed in order to couple the device to the artery. For example, the plates are moved toward each other such that a distance of the inner surfaces of the plates from each other is 0.5-4 mm, e.g., 1-2 mm. For some applications, due to the general opposition of the plates from each other, the artery is gripped by the plates, and does not slide out from between the plates. For some applications, device 80 acts on the artery in a similar manner to that described with reference to devices 60 and 70.

Figure 4A:
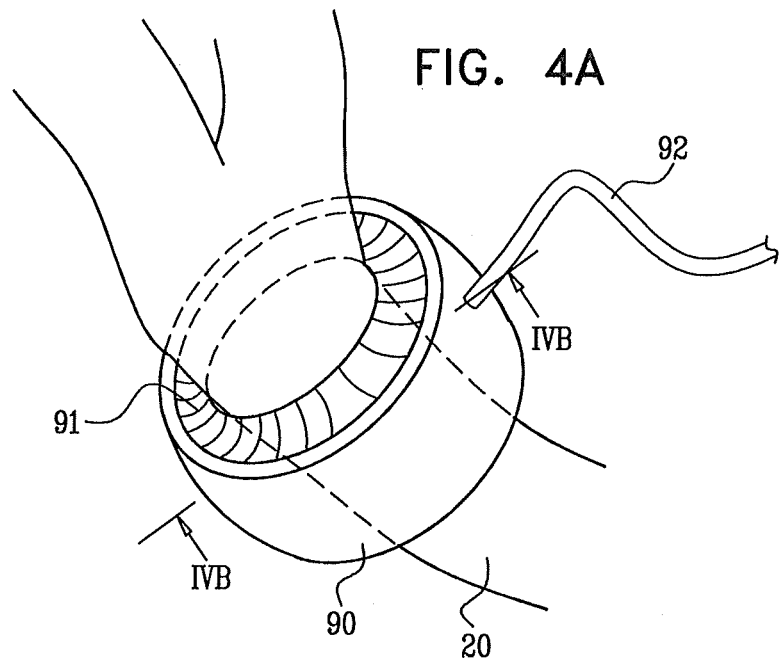
FIGS. 4A-B are schematic illustrations of a rigid shell coupled to an internal inflatable chamber and placed around an artery, in accordance with some applications of the present invention.
Figure 4B:
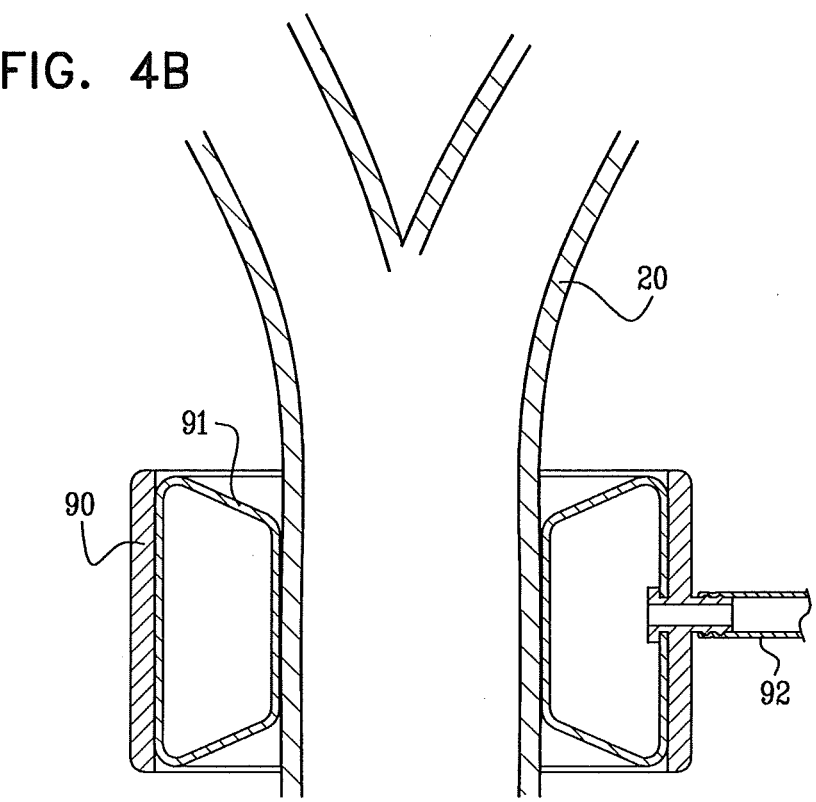

Reference is now made to FIGS. 4A-B, which are schematic illustrations of a rigid shell 90 coupled to an internal inflatable chamber 91 and placed around artery 20, in accordance with some applications of the present invention. Shell 90 and chamber 91 constitute a cuff that is placed around the artery. Chamber 91 is filled with a fluid and is disposed between the shell and the artery. The chamber is typically a sheath that is coupled to the arterial wall with sutures, biological glue, clips, and/or in accordance with other techniques described herein. For some applications, the chamber becomes coupled to the artery due to fibrosis. The chamber transmits the pressure within the chamber to the adjacent arterial wall. A tube 92 supplies the cuff with fluid and enables adjustment of the pressure within the chamber.

For some applications, chamber 91 applies outward forces on the arterial wall during systole, thereby in effect increasing the compliance of the artery. Alternatively or additionally, the cuff applies compressive pressure to the artery. For some applications, coupling the cuff to the artery increases the response of the baroreceptors to pressure changes at low pressures. For some applications, pressure within the chamber is controlled by a control unit. For some applications, the control unit receives inputs such as heart rate, blood pressure, arterial diameter, arterial wall tension, and/or other physiological parameters and regulates the pressure within the chamber in response to the inputs. Alternatively or additionally, the pressure within the chamber is controlled by a passive mechanism, such as that described with reference to FIG. 4C. In accordance with respective applications, the pressure in the chamber is kept constant or is changed, either in a gradual manner or in a pulsatile manner. For example, pressure changes within the chamber may be coordinated with the subject's heart beat.

For some applications, the cuff is filled with a fluid that over time is released into the subject's body, or is actively withdrawn from the subject's body, such that the cuff acts on the artery for only a predetermined period of time.

Figure 4C:
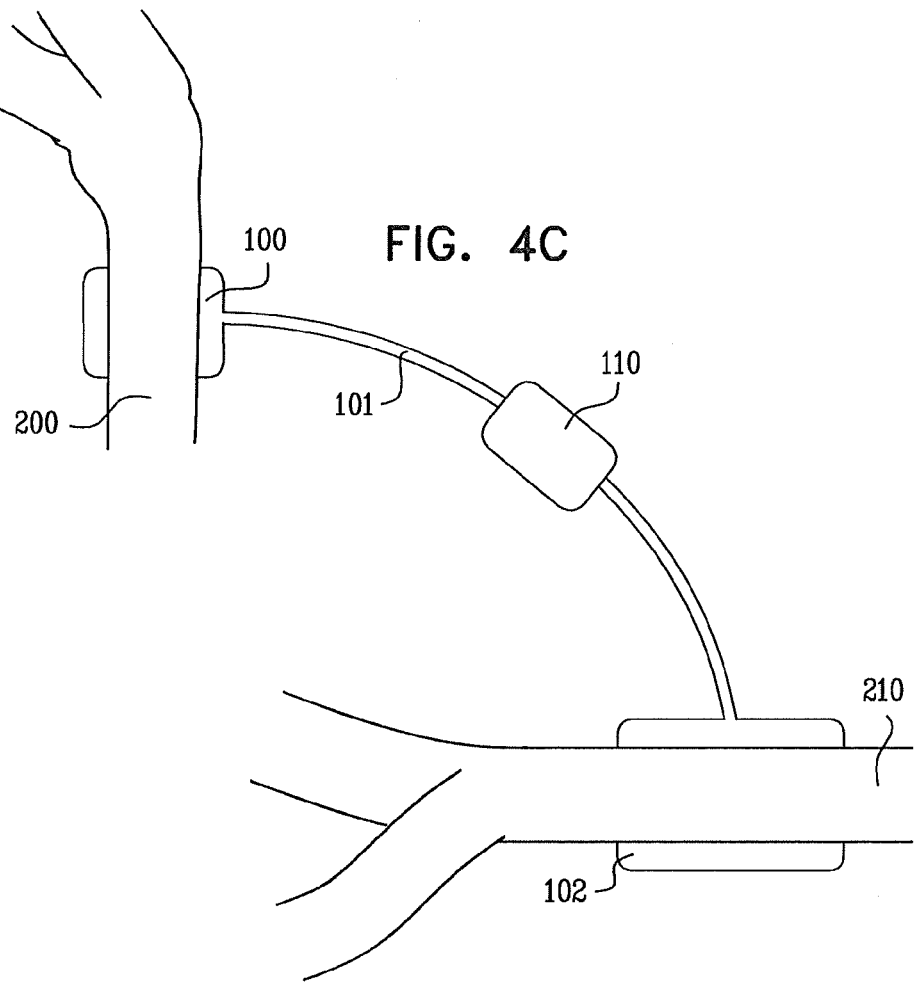
FIGS. 4C-D are schematic illustrations of a system for delivery of pressure from a source artery to a target artery, in accordance with some applications of the present invention.

Reference is now made to FIG. 4C, which is a schematic illustration of a tube 101 for inducing a pressure change around an artery, in accordance with some applications of the invention. For some applications, a pressure cuff 102 is placed around a first artery 210 ("the source artery"), such as the subclavian artery. Tube 101 extends from pressure cuff 102 to the vicinity of a second artery 200 ("the target artery"), such as the carotid artery. At the target artery the tube is connected to a pressure cuff 100 that is placed around the target artery. (For some applications, cuffs 100 and 102 are generally similar to the cuff described with reference to FIGS. 4A-B.) The tube is connected to the pressure cuffs such that the cuffs are in fluid communication with each other via the tube. For some applications, one or both of pressure cuffs 100 and 102 is not placed 360 degrees around the artery. For example, pressure cuff 100 may be placed around only 180 degrees of the circumference of the target artery, in order to facilitate shape-change of the target artery during the subject's cardiac cycle.

As a result of the fluid communication between cuffs 100 and 102, changes in pressure in cuff 102 (due to changes in pressure of source artery 210) cause changes in the pressure of cuff 100, which, in turn, change the diameter and transmural pressure of the target artery. For example, the cuff applies pressure to the target artery, thereby increasing the transmural pressure, and reducing the diameter of the target artery. Generally, the ratio of the pressure change in cuff 102 to the resultant pressure change of cuff 100 depends on the relative volumes and shapes of each of the cuffs and on the systolic and diastolic diameters of the target and source arteries. For some applications, the apparatus is configured such that the ratio of the pressure change in cuff 102 to the resultant pressure change of cuff 100 varies in accordance with the relative lengths of the cuffs. For example, cuff 102 may be longer than cuff 100, and the change in pressure in cuff 102 generates a larger change of pressure in cuff 100, or vice versa.

For some applications, the natural expansion of source artery 210 is harnessed to cause a peristaltic squeezing motion in target artery 200, in order to increase blood flow through the target artery. For example, such a device may be used to increase the blood flow through small blood vessels that are not typically treated by angioplasty or bypass surgery. Such a device may be used to treat small vessel disease, which causes cardiac ischemia and/or peripheral limb ischemia. Alternatively or additionally, such a device is used to increase blood flow into the penis, as a treatment for erectile dysfunction.

For some applications, the expansion of source artery 210 is used to constrict target artery 200, for a short duration during the cardiac cycle. Thus, the flow through the target artery is reduced for a short duration during the cardiac cycle. For example, this may be used to increase blood flow through a third artery, which branches proximal to the target artery. For some applications, this technique is applied in cases in which the subject suffers from, or is suspected of suffering from steal syndrome, in which the flow through the target artery is of lower resistance and thus steals blood flow from the third artery. By partially occluding the target artery during at least part of the cardiac cycle, the blood is diverted to the third artery. For some applications, such a device is used to treat small vessel disease, which causes cardiac ischemia.

For some applications, cuff 102 is applied to a target vein instead of a target artery. The source artery is used to supply pressure to the target vein, in order to increase venous return. For example, the device may be used in cases of venous insufficiency (such as peripheral venous insufficiency) or in cases of reduced lymphatic return, such as the reduced venous return that might occur following a mastectomy procedure. Or, the device may be used to induce retrograde circulation to areas of reduced blood supply, such as ischemic foot wounds, to increase the blood supply to the wound.

For some applications the device may be applied to a target vein that vascularizes the penis, in order to increase the venous pressure in the penis. Increase in the venous pressure of the penis has been shown to maintain rigid erection, to treat erectile dysfunction. For example, see "Implantable penile venous compression device: initial experience in the acute canine model," Paick J., The Journal of Urology 1992, Vol. 148, No. 1, pp. 188-191, which is incorporated herein by reference. For some applications, the device causes a pulsatile increase in venous pressure that is dependent on heart rate and blood pressure. Typically, the device is configured such that the elevation in venous pressure caused by the device does not cause constant erection. Rather, in combination with natural changes associated with sexual arousal (such as increased heart rate and blood pressure), which are typically present even in subjects suffering from erectile dysfunction, the device elevates venous pressure sufficiently to facilitate an erection.

For some applications, cuff 102 is applied to a target renal vein in a subject with increased renal vein pressure, to reduce the renal vein pressure, in order to treat renal insufficiency and improve renal function. For some applications, such a reduction in renal pressure is accompanied by a reduction in aldosterone, renin and angiotensin secretion by the subject, and thereby treats hypertension of the subject. For some applications, cuff 102 is applied to a renal vein of the subject, in conjunction with an implantable valve being implanted in the vein. For some applications, the effect of increased renal venous pressure is in accordance with the effects described in the following articles, which are incorporated herein by reference:

"Effect of increased renal venous pressure on renal function," Doty J. M., The Journal of Trauma: Injury, Infection, and Critical Care: December 1999, Volume 47, Issue 6, p 1000.

"Glomerular ultrafiltration dynamics during increased renal venous pressure," J. R. Dilley, AJP—Renal Physiology, Vol 244, Issue 6 650-F658.

Figure 4D:
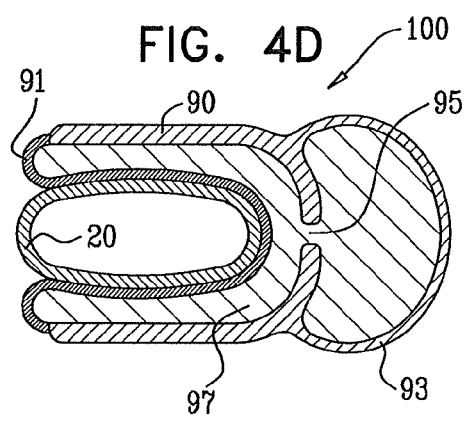

Reference is now made to FIG. 4D, which is a schematic illustration of cuff 100, in accordance with some applications of the present invention. For some applications, cuff 100 on target vessel 200 (as shown in FIG. 4C) is connected to an elastic reservoir 93, for example, via a narrow passage 95 or tube. The cuff is filled with a fluid 97, which typically has high viscoelasticity. The viscoelastic fluid, the passage, and the reservoir act as a shock-absorber that has a characteristic temporal response. During systole, the cuff applies positive pressure to the target artery. The pressure of the cuff on the artery is maximal at initiation of systole, but decreases as fluid passes from the cuff into the reservoir. Upon termination of the systole, the fluid passes back into the cuff, slowly increasing the pressure on the artery. For some applications, a time constant for the system to undergo two-thirds of a transition in its shape (during systole or diastole) is between 75 ms and 200 ms.

For some applications, tube 101 passes through a regulator 110 (as shown in FIG. 4C). The regulator regulates the pressure transferred to target artery 200 from source artery 210. For some applications, the tube extends between the first and second cuffs without passing through a regulator (not shown). In such applications, increases in pressure in source artery 210 cause constriction of target artery 200, which may cause either dampening or enhancement of the baroreceptor activity in the target artery depending on the location of the cuff on the target artery.

Figure 4E:
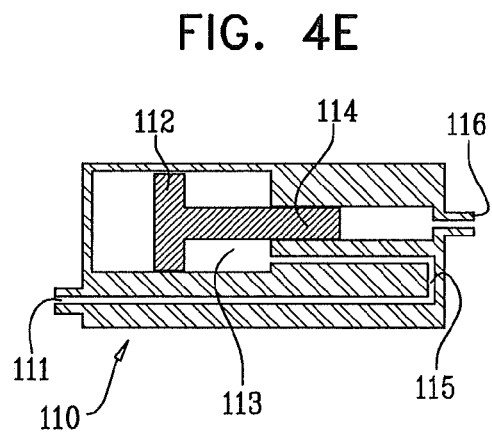
FIG. 4E is a schematic illustration of a regulator unit that is used with the system of FIG. 4C, in accordance with some applications of the present invention.

Reference is now made to FIG. 4E, which is a schematic illustration of regulator 110, in accordance with some applications of the present invention. For some applications, pressure is transferred to the regulator from source artery 210, via tube 101 and a first regulator-inlet 116. The pressure then drives a piston 114. A piston head 112 moves inside a negative-pressure chamber 113, which draws fluid into chamber 113, from cuff 100, via tube 101, a second regulator-inlet 111, and conduit 115. There results a reduction in pressure in cuff 100, which reduces the transmural pressure of target artery 200.

Figure 5A:
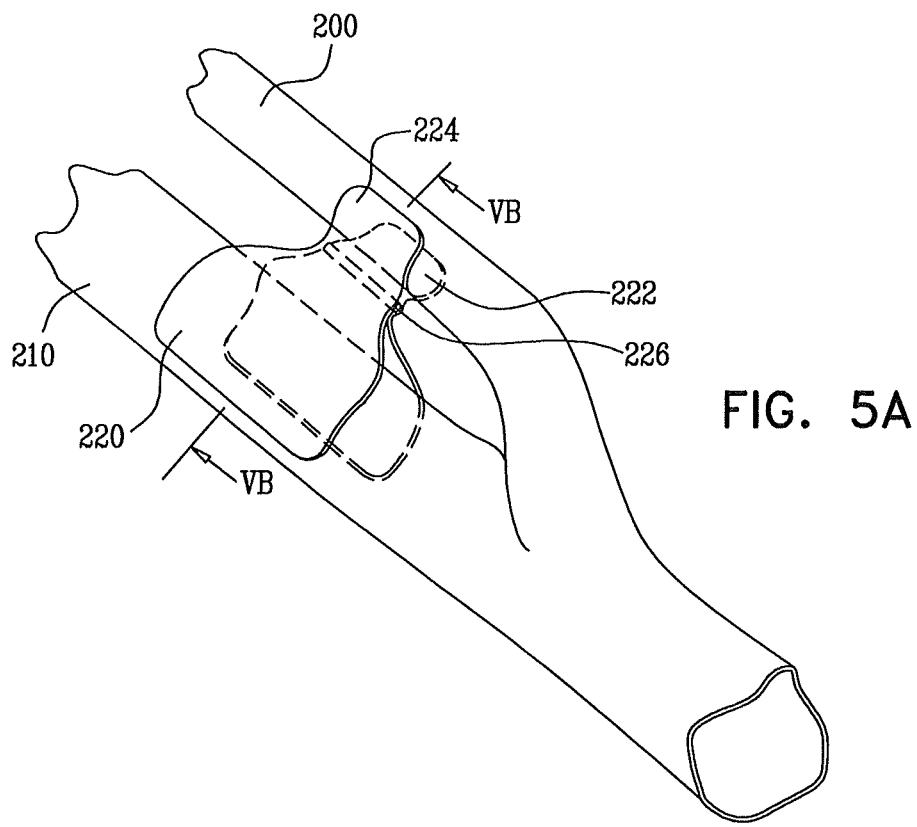
FIGS. 5A-B are schematic illustration of a scissor-action device, in accordance with some applications of the present invention.
Figure 5B:
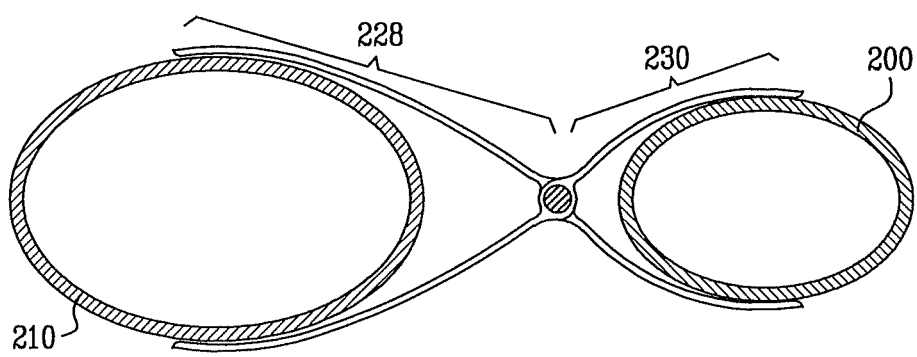

Reference is now made to FIGS. 5A and 5B, which are schematic illustrations of a scissor-action device 220, in accordance with some applications of the present invention. "Scissor-action," in the context of the present application, means the articulation of two members about a joint, each member having two ends, such that when a first end of one of the members is brought closer to a first end of the other member, the respective second ends of the two members are correspondingly brought closer together. "Scissor-action"

does not refer to cutting. For some applications, instead of, or in addition to cuffs 100 and 102, and tube 101, scissor-action device 220 is used for transferring energy between adjacent arteries for producing compression of one of the arteries. The scissor-action device has two arms 222 and 224, crossing at a hinge 226 that is positioned such that there is a long hinged portion 228 on one side of the hinge, and a short hinged portion 230 on the second side of the hinge. (Alternatively, the hinged portions are reversed with respect to short and long as described, or, for some applications, may be of the same length, mutatis mutandis.) The long hinged portion is typically placed around source artery 210, and the short hinged portion around the target artery 200. During systole, a larger outward force is applied to the long hinged portion than to the short hinged portion. Since the long hinged portion is placed around the source artery, the source artery pushes the long hinged portion outwards, thereby causing compression of the target artery by the short hinged portion.

Typically, the precise location of the hinge affects the transfer of forces between the long and short hinged portions. Although, hinge 226 is shown in FIGS. 5A-B as being placed closer to target artery 200 than to source artery 210, for some applications, the hinge is placed further from the target artery than from the source artery. Typically, placing the hinge further from the target artery will cause a greater compression of the target artery than if the hinge is placed closer to the target artery. Alternatively, the hinge is placed at approximately an equidistant point from the target and source arteries, or, as shown in FIGS. 5A-B, the hinge is placed closer to the target artery than to the source artery.

Reference is now made to FIG. 6A, which is a schematic illustration of a longitudinal stretch device 300 placed on artery 20, in accordance with some applications of the present invention. The device includes a rod 303 which is connected to the arterial wall at two points via connectors 302. The rod pushes the connectors apart in the longitudinal direction, increasing axial tension within the arterial wall. For some applications, increasing axial tension within the arterial wall increases baroreceptor responsiveness to regular stimuli, in accordance with the article: "Theoretical and electrophysiological evidence for axial loading about aortic baroreceptor nerve terminals in rats," Feng B, Am J Physiol Heart Circ Physiol. 2007 December;293(6):H3659-72, which is incorporated herein by reference. For some applications, the rod includes an elastic portion 301 and the length, elasticity, and/or shape of the elastic portion is adjusted to regulate the force that the rod exerts on the artery. For some applications, during implantation of device 300, the artery is actively longitudinally stretched. While the artery is stretched, connectors 302 are connected to the artery. Subsequently, the rod maintains the connectors at a fixed minimum distance from each other. Thus, even when the artery is no longer being actively stretched, device 300 maintains the artery in a longitudinally stretched state.

Reference is now made to FIG. 6B, which is a schematic illustration of longitudinal stretch device 300 placed on artery 20, in accordance with some applications of the present invention. For some applications, rod 303 is connected to the artery using rings 304 that are placed around the artery. For some applications, using rings to connect the rod to the arterial wall results in the forces generated by the rod being equally distributed around a large area of the arterial wall. For some applications, three or more rods connect the rings. For some applications, the rings are connected to the rods in such a way that ring expansion during systole causes elongation of the rods and increased longitudinal tension.

Reference is now made to FIGS. 7A-B, which are schematic illustrations of a passive compression ring 503 placed around artery 20, in accordance with some applications of the present invention. The passive compression ring has a bulge 504 at one end of the ring. As the ring expands due to the expansion of the artery during systole (FIG. 7B), the bulge pushes element 505 into the arterial wall, compressing the artery. The extent of arterial compression is a function of the shape of the ring and its elastic properties, among other factors.

For some applications, the implanted devices described herein are coated with a drug-eluting coating to inhibit tissue overgrowth over the device. Alternatively or additionally, the implanted devices are radioactive, to inhibit tissue growth over the device. For some applications, the devices are coated with a coating that increases fibrosis in the vicinity of the device, in order to facilitate attachment of the device to the artery.

For some applications, the implanted devices are biodegradable, for example, having an effective half life of 1-7 days, or 1-12 weeks. In such applications, the devices are used for short-term use, the devices typically helping the body "reset" the baroreceptors, such that even after the device has essentially ceased to function, the subject's baroreceptor activity has improved. For example, one or more of the devices described herein may be configured to stretch the artery in the vicinity of baroreceptors, and to change the diameter of the artery. Once the artery is stretched to a larger diameter, the wall pressure in the arterial wall increases and the baroreceptor sensitivity is increased. For some applications, the artery maintains the new, larger diameter (and, optionally, the baroreceptor sensitivity remains increased) even after the removal or the biodegradation of the device. This is akin to a shoe-stretcher, which is placed inside a shoe and is then removed once the shoe is stretched. The shoe remains stretched even after removal of the shoe-stretcher. For some applications, a device is coupled to an artery temporarily (but typically for at least two days), in order to irreversibly alter compliance of the artery in the vicinity of baroreceptors. Subsequently, the device is removed from the artery, or the device biodegrades. For some applications, a device (such as an expandable stent) is temporarily placed inside the artery in order to irreversibly alter the compliance of the artery.

Although applications are described according to which a device as described herein is biodegradable, the scope of the present invention includes a device having a component thereof which is biodegradable. For example, the portion of the device that couples the device to a blood vessel may be biodegradable. Alternatively or additionally, the biodegradable component may biodegrade, reducing forces applied by the device to the blood vessel, while the device itself remains itself at the blood vessel site.

Alternatively, a device is used that is not biodegradable, but that is implanted for only a short time period, such as for 1 to 3 months, and is subsequently explanted. Further alternatively, the device remains intact but, after a given time, the device does not apply any forces (or applies significantly lower forces) to the artery, since the artery has changed to a different diameter or geometry.

For some applications, the properties of an artery are changed by applying a device for only a short period of time (such as a period of seconds to minutes), to change the geometry and/or dimensions of the artery. For some applications, an angioplasty balloon is inflated inside the artery to change the diameter of the artery. For some applications, a balloon is used that is not circular, but rather elliptical. Inflation of the elliptical balloon inside the artery elongates the artery along one axis while substantially not elongating the artery along another axis.

For some applications, properties of the artery are changed by applying heating, laser energy, electrocoagulation, RF energy, and/or another form of energy to the artery. For some applications, properties of the artery are changed by stripping parts of the adventitia of the artery, thereby reducing the tensile force of the artery and increasing the arterial diameter. For example, the adventitia is stripped at 6 and 12 o'clock positions around the circumference of the artery, in order to change the circumferential properties of the artery. Alternatively or additionally, properties of the artery are changed by injecting (e.g., locally injecting) biologically active substances such as smooth muscle relaxants (e.g., botulinum toxin, papaverin, and/or collagenase) into the arterial wall. Further alternatively or additionally, properties of the artery are changed by injection into the arterial wall of a biologically-inert material (such as glass beads, and/or silicone gel), and/or dermal filler material (such as hyaluronic acid, and/or collagen). For some applications, the injected material undergoes degradation with time and leaves the artery wall more relaxed once the material is gone. Alternatively, the material stays in place and causes changes in the properties of the artery. Typically, the properties of the subject's arterial wall are changed in the vicinity of baroreceptors, in order to irreversibly alter the compliance of the artery, by causing a change in the shape of the artery, and/or by causing the artery to undergo a greater change in shape than it would otherwise undergo, over the course of the cardiac cycle. Further typically, this increases baroreceptor stimulation of the subject, and reduces hypertension of the subject. For some applications, the properties of the arterial wall are changed by treating the artery itself, regardless of any presence of plaque on the arterial wall.

For some applications, properties of the arterial wall are changed as described in the paragraph above. For example, the tensile force of the arterial wall is reduced. Subsequently, a device, as described herein, is implanted on the arterial wall. In accordance with the techniques described herein, the device causes changes in the shape of the arterial wall. By applying the device to an arterial wall, the tensile force of which has been reduced, the device causes the arterial wall to undergo a greater shape change than the wall would undergo if the arterial wall properties had not been changed.

For some applications, one or more of the devices described herein are used to reduce the tension of an artery around which they are implanted. For some applications, the devices reduce the tension by reducing expansion of the artery (e.g., during systole), relative to expansion of the artery in the absence of the device. For some applications, such devices are used after vascular surgery to reduce the tension in newly repaired arteries, such as after a carotid endarterectomy, in order to promote healing, reduce the risk of leak and dissection, and/or to prevent post-procedural hypotension.

For some applications, a method for treating a subject suffering from hypertension comprises the following steps:

(a) Identifying that the subject suffers from hypertension, typically by taking at least three blood pressure measurements.

(b) Testing the baroreceptor sensitivity of the subject, for example, by creating a baroreceptor pressure-response curve (similar to that of FIG. 1B). The required data may be acquired by measuring the change in the subject's heart rate, or R-R interval, in response to spontaneous blood pressure changes, or blood pressure changes in response to a pharmacologic challenge (such as a blood pressure increase by administration of Phenylehrine, Norepinephrine, etc.). For some applications, a baroreceptor response is determined without generating a baroreceptor pressure-response curve. For example, a physician may determine the subject's R-R interval at one or more blood pressures of the subject, without actually plotting a baroreceptor pressure-response curve.

(c) Implanting one or more of the devices described herein if the subject is found to suffer from hypertension with reduced baroreceptor sensitivity.

For some applications, a method is provided for treating hypertension in situations in which the subject has an indication for vascular surgery (such as carotid or coronary obstruction to flow). The surgery is performed to treat the obstruction, and a device as described herein is implanted on a treated artery or on an artery within the surgical field, to treat the hypertension.

For some applications, a method is provided for evaluating the appropriateness of the device localization and function. The method includes:

(a) Placing in a subject's body a device which modulates arterial mechanical properties and/or baroreceptor responsiveness. Typically, the device includes a device as described herein.

(b) Allowing for stabilization of the subject's cardiovascular system over a period of time.

(c) Acquiring physiological data from the subject which enables calculation of the baroreceptor sensitivity or creation of a baroreceptor pressure-response curve (such as that of FIG. 1B). Such data may be acquired by measuring the change in heart rate or R-R interval in response to spontaneous blood pressure changes, or blood pressure changes in response to a pharmacologic challenge (such as a blood pressure increase by administration of Phenylehrine, Norepinephrine, etc.). For some applications, a baroreceptor response is determined without generating an actual baroreceptor pressure-response curve. For example, a physician may determine the subject's R-R interval at one or more blood pressures of the subject, without actually plotting a baroreceptor pressure-response curve.

(d) Comparing the change in baroreceptor sensitivity or pressure-response curve to an expected change.

(e) Repositioning the device at different locations in the subject's body, repeating steps (a) to (d) at each of the locations, and then comparing the results in order to determine how best to place the device.

Although applications are described, according to which vessel 20 is an artery, the scope of the present invention includes using the devices described herein with another blood vessel, for example, a vein. For some applications, one or more of the devices described herein are used to increase the wall tension in generally tubular organs of a subject, other than blood vessels, such as organs of the gastrointestinal tract or nerves. For some applications, when applied to organs of the gastrointestinal tract the increased wall tension causes an increased feeling of satiety, which may be used, for example, to reduce a subject's food intake, to treat obesity. For example, the devices described herein (such as the devices described with respect to FIGS. 3E-F) may be placed around the stomach, the duodenum or the small intestine, so as to enhance the rise in pressure in these portions induced by a meal, thus causing reduction in food intake. For some applications, the devices described herein are applied to the subject's rectum or sigmoid colon wall, to enhance wall tension and induce defecation upon fullness, to treat constipation. For some applications, the devices described herein are used to stretch a nerve in a controlled fashion, to help reduce conduction of the nerve to alleviate pain, such as neuropathic pain.

For some applications, the devices described herein are used to cause a reduction in wall tension of a tubular structure of a subject. For some applications, such a reduction in the wall tension is applied to organs of the gastrointestinal tract following a surgical procedure, for example, to reduce the tension at a surgical anastomosis, to promote healing of the anastomosis. For some applications, the devices reduce tension in the wall by applying inward forces to the wall, such that the wall expands by a smaller amount (e.g., as food passes through the structure) than in the absence of the device. For some applications, one or more biodegradable devices are implanted near an anastomosis, and the devices biodegrade at a time by which the anastomosis has healed.

For some applications, one or more of the devices described herein is implanted within an artery or another hollow organ of the body. For example, the devices shown in FIGS. 2A, 2B, 6A, and/or 6B may be adapted for implantation in an artery. When implanted within arteries, the devices increase the baroreceptor sensitivity as described, and/or induce other effects as described.

For some applications, one or more of the devices described herein is implanted within a vein in a vicinity of a valve, and the devices are used to increase the potency of the valve by stretching the vein longitudinally. Stretching the vein longitudinally reduces the diameter of the vein, thus allowing the valve leaflets to cover more of the diameter of the vein, and reducing the degree of regurgitation through the vein.

For some applications, the devices described herein are used to divert emboli traveling up the common carotid artery toward the external carotid artery. The embolic load through the internal carotid artery is thus reduced, protecting the brain from embolic damage, such as embolic stroke. For such applications, the device, or a portion of the device (such as the portion that couples the device to the blood vessel) is degradable, and is designed to function for a short period of time, for example, 2 to 48 hours. Typically the device will be placed around the artery for a period of time during which there is an increased risk of emboli flowing via the carotid artery. Such periods of time include the hours or days immediately following carotid artery stenting or endarterectomy, and the time during, and immediately following, other large vascular surgeries, such as aortic aneurysm repair, or coronary artery bypass grafting.

For some applications, a device is coupled to both the external and the internal carotid arteries, such that it modulates the angle between the arteries. For some applications the angle between the external and internal carotid arteries is modulated such that emboli are diverted toward the external carotid artery. The internal carotid artery is a direct continuation of the common carotid artery, whereas the external carotid artery branches from the common carotid artery. Therefore, emboli have a natural tendency to flow from the common carotid artery into the internal carotid artery. For some applications, a device is positioned such that it generates turbulent flow at the bifurcation of the external and internal carotid arteries, which overcomes the natural tendency of emboli to flow toward the internal carotid artery. Typically, one of the devices described herein is implanted in the vicinity of the carotid bifurcation in order to generate the turbulent flow.

Alternatively or additionally, a device is placed so as to temporarily reduce the flow through the internal carotid artery (typically, by reducing the diameter of the internal lumen by no more than 60% of its natural diameter), in order to divert emboli toward the external carotid artery. For example, a device may be placed outside or inside the internal carotid for a period of less than 30 days after carotid and/or heart surgery. The device prevents the restoration of 100% flow for the period that the device is implanted, in order to reduce the likelihood of emboli to the brain.

For some applications, the devices described herein are remotely activated and/or deactivated to apply or relieve the forces on the artery. For some applications, the device comprises a biodegradable timer component. Once the timer component dissolves, the forces applied to the artery are diminished. Alternatively, the timer component prevents the device from beginning its operation until after a certain time period has passed, at which point forces that were previously prevented from reaching the artery are now applied to the artery. For some applications, such delayed activation is used after carotid surgery, to withhold applying forces to the artery in the immediate post-surgical period. Alternatively, the device applies the force to the artery only in the post-surgical period, to prevent perisurgical blood pressure swings. For example, the device applies force to the carotid artery, to neutralize the baroreceptor response of the carotid artery, by constricting movement of the carotid artery. For some applications, the device applies the force to the carotid artery in order to stabilize the subject's blood pressure in the perisurgical period, and subsequently (e.g., after one to two months) the device biodegrades and the body's regular blood pressure control is resumed.

For some applications, the application of forces to the artery is controlled by an element that can be externally controlled. For example, the element may be a balloon that can be inflated or deflated from outside of the body. For some applications, once inflated, the balloon reduces force applied by the force-applying parts of the device to the artery, thus eliminating application of forces to the artery. (For example, if the force-applying parts are on respective side branches of a V-shaped device, then the balloon could be placed inside the V, at the joint of the two side branches.) Alternatively, when inflated, the balloon bridges between the artery and the device, thus facilitating application of forces to the artery. For some applications, the device is deactivated from outside the subject's body using a magnetic deactivation unit that releases a pin that causes a balloon to leak, thereby terminating the effect of the device.

For some applications, the device is externally activated or deactivated, and an intermittent activation is applied, with the ON and/or OFF intervals typically being days or weeks. For some applications, two such devices are implanted in a human subject, for example, in left and right arteries. For some applications, the devices are activated in an intermittent fashion, with only one device actively applying forces to an artery at each given time.

For some applications, the degree of force applied to the artery is controlled and can be changed from zero to a maximum in a gradual fashion. For example, this may be done using a subcutaneous self-sealing reservoir. Fluid is conveyed to the device via the reservoir, or withdrawn from the device via the reservoir, in order to control the pressure within the reservoir and thereby achieve a desired level of baroreceptor control. For some applications, such a self-sealing reservoir is used to regulate the baroreceptor control of the device. For example, in response to the measured blood pressure of the subject, a physician may regulate the baroreceptor control of the device via the self-sealing reservoir at intervals of several days, weeks, or months. Alternatively or additionally, the self-sealing reservoir is used for deactivating the device by fluid being withdrawn from the reservoir.

Figure 8:
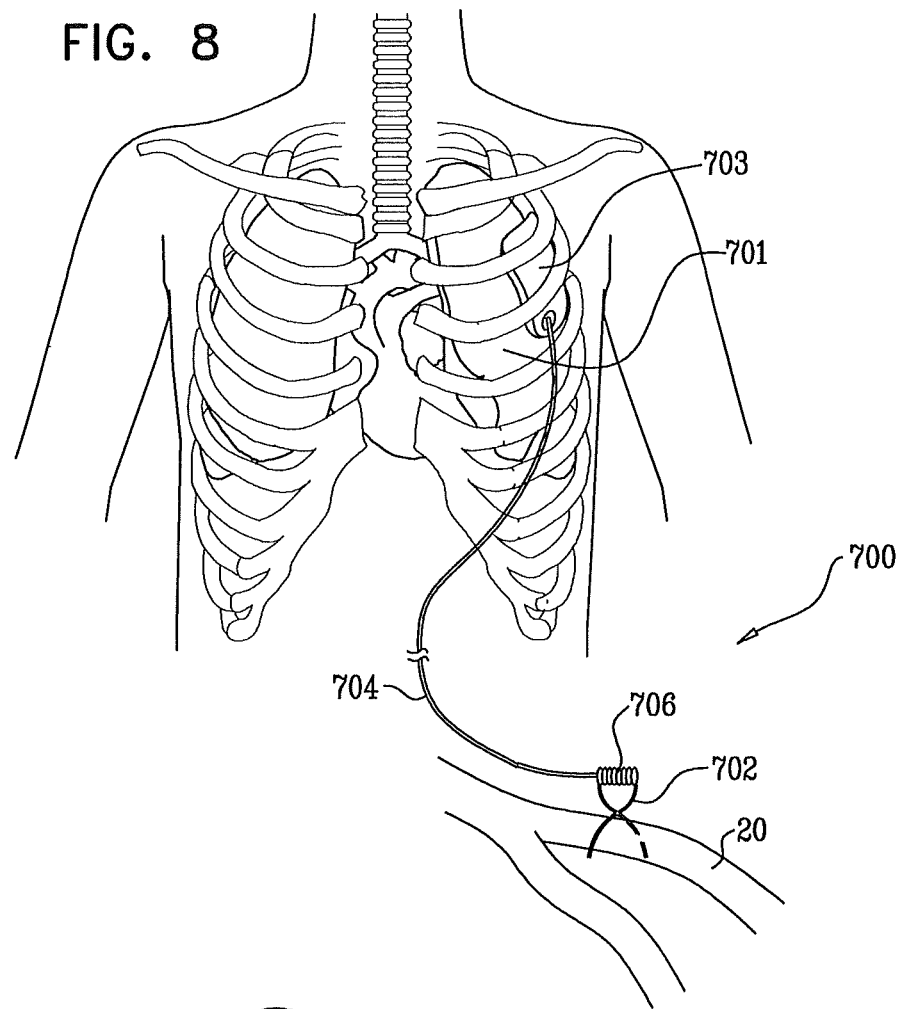
FIG. 8 is a schematic illustration of a device for harnessing negative pressure of the subject's pleural cavity, in accordance with some applications of the present invention.

Reference is now made to FIG. 8, which is a schematic illustration of a device 700 for harnessing negative pressure of the subject's pleural cavity 701, in accordance with some applications of the present invention. Device 700 is typically placed in pleural cavity 701. For some applications, the negative pressure produced in the pleural cavity during normal breathing is harnessed to affect the baroreceptors. For example, the negative pressure may be used to expand a device (such as cuff 100, shown in FIG. 4c) that is coupled to the outside an artery. For some applications, a pleural-cavity chamber 703 that contains a fluid (e.g., saline) is placed in the pleural cavity. A tube 704 couples the pleural-cavity chamber to a pressure chamber (e.g., cuff 100, shown in FIG. 4C) that is disposed around an artery such that the pleural-cavity chamber is in fluid communication with the pressure chamber that is disposed around the artery.

For some applications, a structure made of rigid movable elements 702 is inserted into tissue surrounding artery 20. For example, the movable elements may be inserted into tissue surrounding the carotid sinus. The negative pressure from the pleural cavity is used to increase the distance between the movable elements, thus applying outward forces on the sinus walls. For example, as shown, the negative pressure may be conveyed to the movable elements, via tube 704 and a bellows-device 706. The pleural cavity passes from negative to positive pressures during the respiration cycle. For some applications, a valve is placed inside the tube, such that only either negative pressure or positive pressure of the pleural cavity is transferred to the artery. For some applications, positive pressure is transferred from the pleural cavity to the movable elements, in order to compress the carotid sinus. For some applications, positive and negative pressure is transferred from the pleural cavity to the carotid sinus. Thus, the pressure applied to the sinus by the movable elements is cyclical, varying from positive to negative.

Figure 9A:
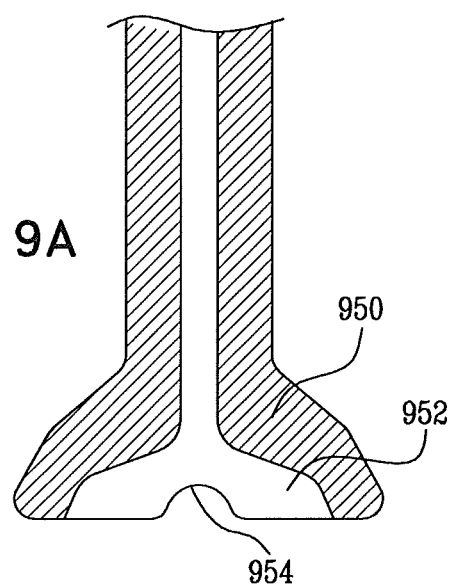
FIGS. 9A-C are schematic illustrations of a device for facilitating the suturing of an artery, in accordance with some applications of the present invention.
Figure 9B:
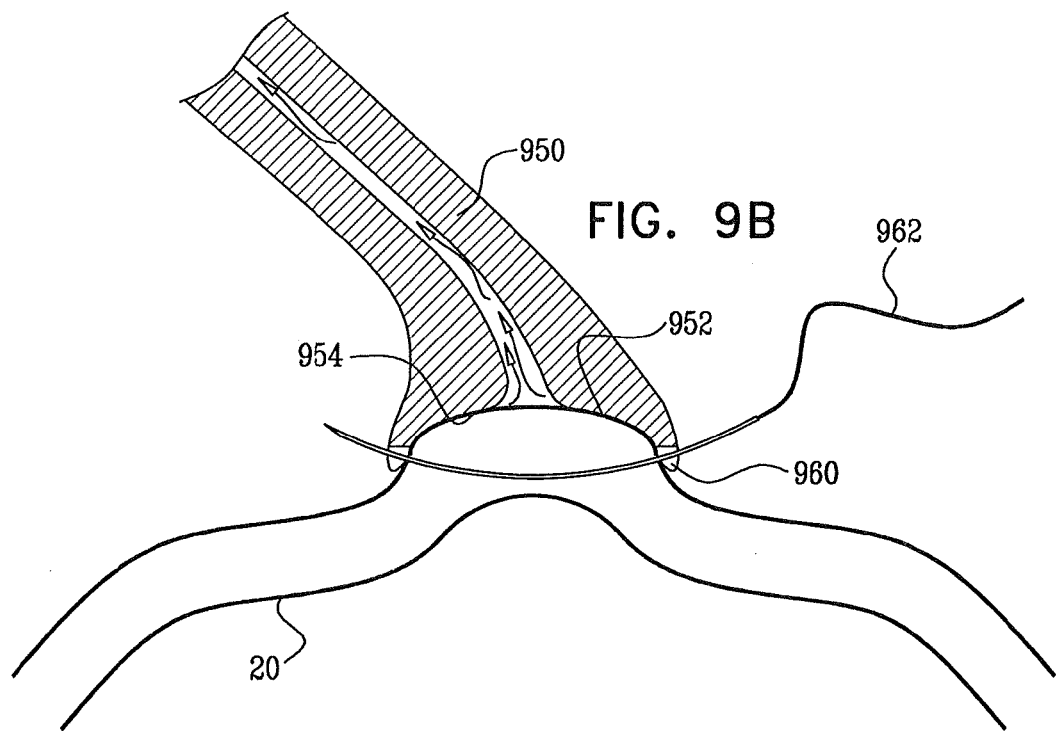
Figure 9C:
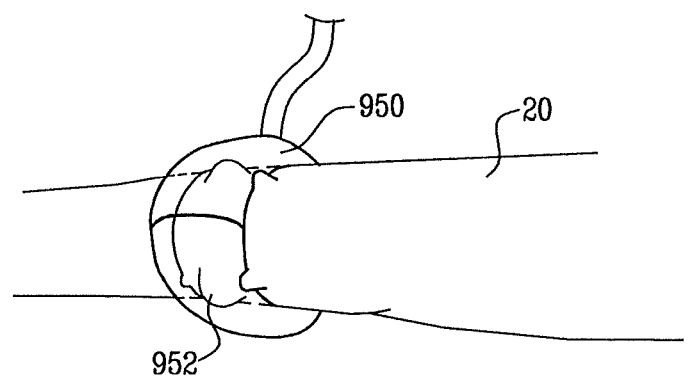

Reference is now made to FIGS. 9A-C, which are schematic illustrations of a device 950 for facilitating the suturing of artery 20, in accordance with some applications of the present invention. For some applications, the devices described herein are sutured to the outside of an arterial wall. When using sutures to attach a device to the arterial wall, it is typically desirable that sutures are applied through the media but not through the intima of the artery. Device 950 facilitates the application of a suture to a predetermined depth.

For some applications, device 950 facilitates the identification of local points on the arterial wall as being rich in baroreceptors. Prior to using device 950 to apply sutures to the artery, the device is used to apply suction to the arterial wall at a plurality of local points on the arterial wall. Changes to the subject's baroreceptor sensitivity, in response to the suction being applied to respective local points, are monitored, in accordance with the techniques described herein (e.g. by determining the subject's R-R interval). Local points are identified as being baroreceptor rich, by determining that suction being applied to those points increases the subject's baroreceptor response and/or sensitivity. Subsequently, the device facilitates suturing of the devices described herein to the identified local points of the arterial wall.

Device 950 includes a suction cup 952 with a concave surface 954. When placed on artery 20, suction causes the artery wall to enter the cup to a predetermined depth, such that the artery wall is brought into contact with surface 954. For some applications, a suction cup is placed on a portion of the arterial wall that is identified as being baroreceptor rich (e.g., as described in the previous paragraph). A suture 962 is passed through the portion of the arterial wall that has been suctioned into the suction cup, via a hole 960 in the suction cup. For some applications, the suture is passed through the depression manually. Alternatively, the device has a mechanism for pushing the suture along a predetermined route. For some applications, device 950 is made of two parts and is placed around the whole circumference of the artery to facilitate suturing of up to the full circumference of the artery, as shown in FIG. 9C. For some applications, the device expands the artery to an increased diameter by applying suction to the arterial wall. A device is sutured to the arterial wall while the wall is in the expanded state. The device inhibits contraction of the artery from the expanded state of the artery, thereby increasing the effective compliance of the artery, relative to the arterial compliance in the absence of the device.

Figure 10A:
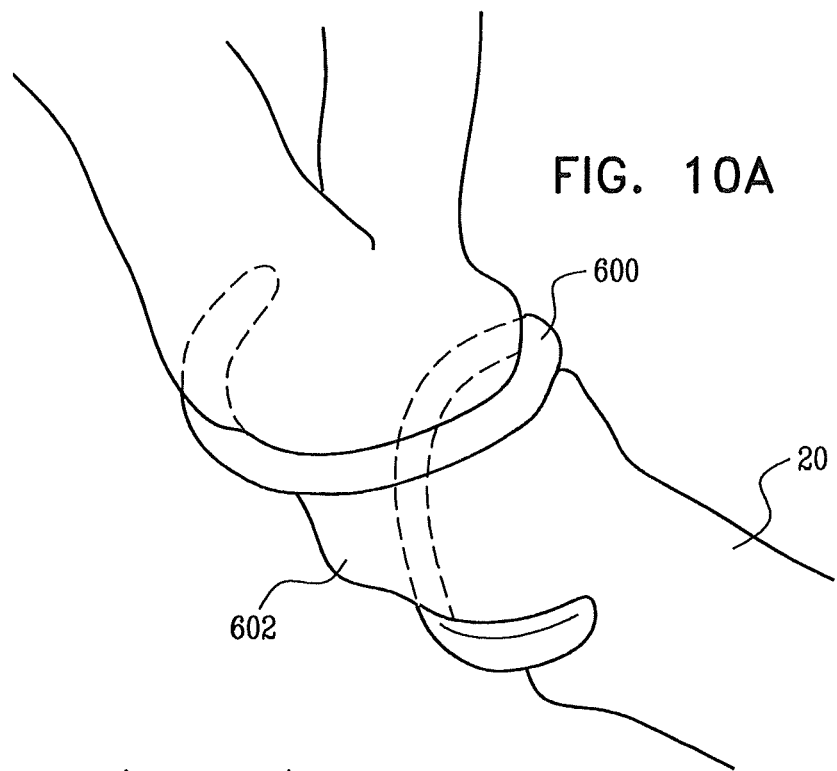
FIGS. 10A-B are schematic illustrations of a spiral structure placed around an artery, in accordance with some applications of the present invention.
Figure 10B:
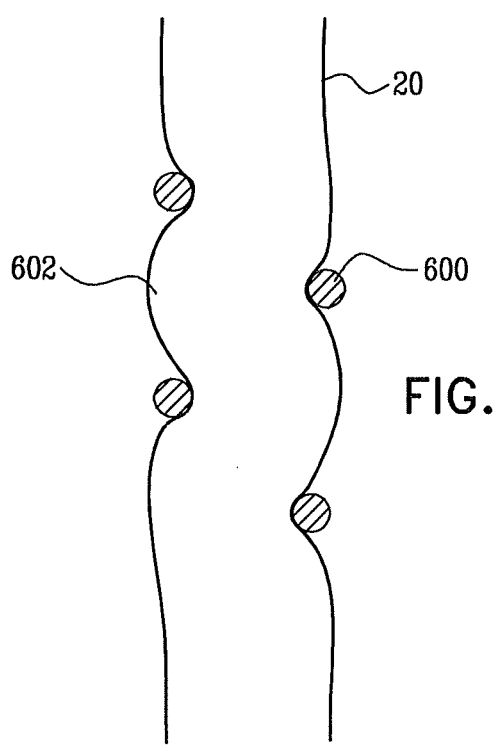

Reference is now made to FIGS. 10A-B, which are schematic illustrations of respective views of a spiral structure 600 placed around artery 20, in accordance with some applications of the present invention. For some applications, a device is placed on the arterial wall that passively (i.e., without the device needing to undergo a shape change) causes the artery to undergo a greater change in shape over the course of the cardiac cycle than the artery would undergo in the absence of the device. For example, spiral structure 600, or a differently shaped structure, may be placed on the arterial wall in order to cause the artery to act in this manner. As shown in FIGS. 10A and 10B, arterial pulsations cause portions 602 of the arterial wall to bulge between parts of the spiral structure. This causes local deformation and stretching of the arterial wall in several regions, which typically causes baroreceptors at those regions to increase their activity.

For some applications, the structure is coupled to the arterial wall with sutures, biological glue, clips, and/or in accordance with other techniques described herein. For some applications, the structure is specifically designed to fit over a bifurcation such as a bifurcation of the internal and external carotid arteries. For some applications, the shape and elastic qualities of the spiral structure are regulated, in order to regulate the changes in the subject's baroreceptor activity. For example, characteristics of the spiral structure may be regulated prior to implantation of the device, or in real time, while the device is on the arterial wall, in order to regulate the changes in baroreceptor activity.

For some applications, the devices described herein are configured to induce only minimal (if any) reduction in blood flow through the artery coupled to the device. For some applications, such minimal reduction in flow is achieved by applying forces to the artery along a short segment of the artery only (e.g., less than 1 cm). Alternatively or additionally, minimal effect on flow is achieved by maintaining an internal diameter of the artery, in the presence of the device, that is at least 30% of the diameter of the artery, in the absence of the device, throughout the cardiac cycle. Further alternatively or additionally, minimal effect on flow is achieved by maintaining the cross sectional area of the artery, in the presence of the device, to be at least 20% of the cross sectional area, in the absence of the device, throughout the cardiac cycle.

For some applications, the flow through the artery to which the device is coupled is monitored during the implantation of the device, and the device is configured to not reduce the flow by more than 15%. For some applications, the degree of force applied to the artery, and/or a physical distance between parts of the device, is modulated until the measured flow is not reduced by more than 15%. For some applications the absolute minimal distance across the artery (for example, the minor axis of the ellipse of an elliptical device) is limited to no less than 1.5 mm.

For some applications, a device is placed on the subject's external carotid artery and improves blood flow through the subject's internal carotid artery. For some applications, the improvement in flow is achieved by diverting blood flow from the external carotid artery to the internal carotid artery. For some applications, a device is placed on the subject's internal carotid artery (for example, on the carotid sinus), and improves blood flow through the subject's internal carotid artery. For some applications, the improvement in flow is achieved by reducing the turbulence of flow through the portion of the artery on which the device is placed, and increasing laminar flow through the portion of the artery, for example, by using a device as described with reference to FIG. 11A.

Figure 11A:
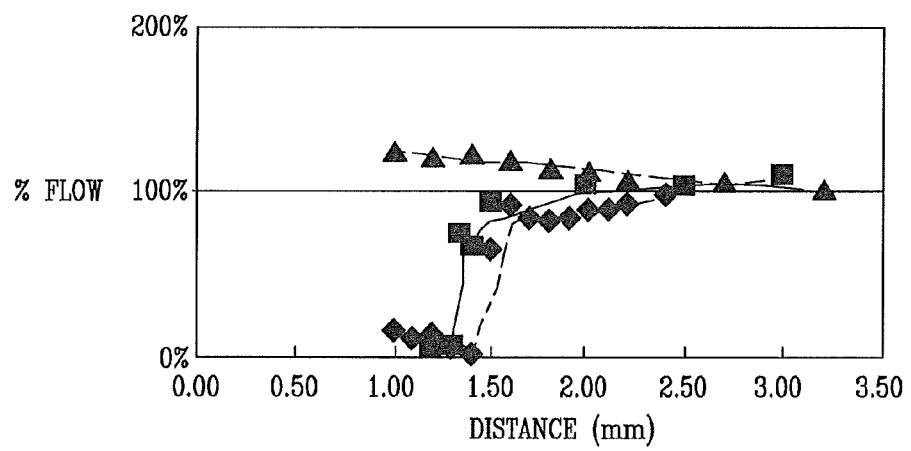
FIG. 11A is a graph showing an increase in flow through the internal carotid artery when a device was placed on the carotid sinus, in accordance with some applications of the present invention.

Reference is now made to FIG. 11A, which is a graph showing an increase in flow through the internal carotid artery when a device was placed on the carotid sinus, in accordance with some applications of the present invention. An adult dog was placed under full anesthesia. A thin blade (width 1 mm, length 3 mm, height 3 mm) was placed over the dog's carotid sinus, in parallel with the direction of flow. The blade was pressed against a rigid plate placed underneath the artery, so that the distance between the blade and the plate was gradually reduced from 3.2 mm to 1 mm. When the blade and the plate were at each of the measured distances from each other, blood flow through the internal carotid was measured for one minute and the average flow rate over that one minute was calculated. The triangles on the graph show the flow through the internal carotid artery, plotted against the distance between the blade and the plate. It may be observed that as the gap between the blade and the plate decreased there was an increase in the rate of blood flow. The increase in blood flow was such that, relative to when no device was placed on the artery, there was approximately a 24% increase in flow when the distance between the blade and the plate was reduced from 3.2 mm to 1 mm. Also shown on the graph are the results obtained from squeezing the carotid sinus between two smooth metal plates (results plotted as squares) and between two non-smooth substantially planar metal plates (results plotted as diamonds). It may be observed that when the carotid sinus was squeezed between plates, the rate of blood flow through the internal carotid artery decreased as the distance between the plates decreased.

The footprint of a device is the area that actually comes into forceful contact with the artery. The inventors hypothesize that the footprint of the device is important for minimizing unwanted effects of a device on blood flow, and/or unwanted biological effects of a device on the arterial wall. For some applications, the footprint of a device is composed of narrow, longitudinal, strip-like components that are oriented in parallel to the artery. Typically, the presence of such components reduces turbulent blood flow, and increases laminar blood flow through the artery. Thus, the presence of such components increases the rate of blood flow through the artery, as described hereinabove. It is noted, however, that for some applications, a device is used that has a footprint that is composed of portions that are oriented substantially perpendicular to the artery. For some applications, the footprint of the device includes several focal points, each of less than 1 square mm, and separated from each other by at least 0.5 mm.

For some applications, a device forces parts of the artery into one or more planes that have a radius of curvature that are much larger than the original radius of curvature of the artery (defined by the actual radius of the artery). For example, a portion of the artery may be compressed such that the portion adopts a shape that is a flat plane, i.e., such that the portion has a radius of curvature that is almost infinite. Typically, a planar surface of the device applies pressure to the artery, such that, at the region of contact between the device and the arterial wall, the arterial wall adopts a planar shape. For some applications, the planes extend around a device, having a footprint, which presses the artery. For example, the footprint of a device may apply pressure to an artery at a pressure region, such that flat planes are formed on the arterial wall in an area adjacent to the pressure region.

The inventors have observed that the activity of the baroreceptors at the carotid bifurcation is best preserved when the lateral aspect of the carotid bifurcation is not dissected from the surrounding tissues and care is taken to avoid dissection of the tissues lying in between the internal and the external carotid arteries. Some of the devices described herein (for example, those described with reference to FIGS. 3A-F) can be applied to the carotid baroreceptors without the need for dissection of the lateral aspects of the bifurcation or of tissues in between the internal and external carotid arteries. (This discussion notwithstanding, the scope of the present invention includes performing such dissection, if appropriate.)

For some applications, a device presses on the artery using two or more planar or curved surfaces, but does not press on the artery from 360 degrees. For some applications, full circumferential pressure on the artery is avoided, with at least one side of the artery not having external pressure applied thereto.

For some applications, the device is positioned over the carotid sinus by the device squeezing the sinus from opposing sides of the sinus, to prevent the sinus from slipping away from the device, e.g., using arms 72 of U-shaped device 70 (described with reference to FIG. 3D). For some applications, the level of squeezing is limited by having a minimal allowed distance between two opposing surfaces of the device.

Figure 11B:
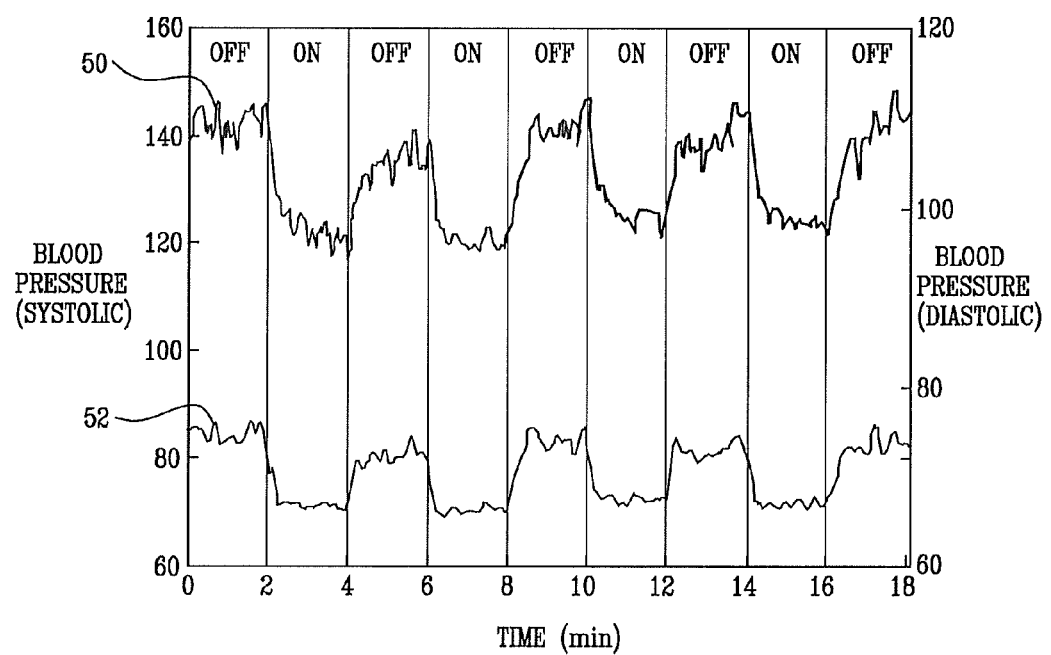
FIG. 11B is a graph showing a reduction in blood pressure when a device was placed on the carotid sinus, in accordance with some applications of the present invention.

Reference is now made to FIG. 11B, which is a graph showing the change in a dog's blood pressure resulting from compressing the dog's carotid sinus, using the blade described with reference to FIG. 11A. These results were obtained from an animal different from the animal used to obtain the results shown in FIG. 11A. However, the device was placed in a position similar to the position of the device used for generating the graph of FIG. 11A. The sinus was compressed at times t=2-4 minutes, 6-8 minutes, 10-12 minutes, and 14-16 minutes. It may be observed that the mean systolic and diastolic blood pressures of the animal, plotted respectively, as lines 50 and 52, dropped when the sinus was compressed. Thus, the blade reduces blood pressure by stimulating baroreceptors of the internal carotid sinus (as demonstrated in FIG. 11B), without reducing blood flow through the subject's carotid arteries (as shown in FIG. 11A).

Figure 12A:
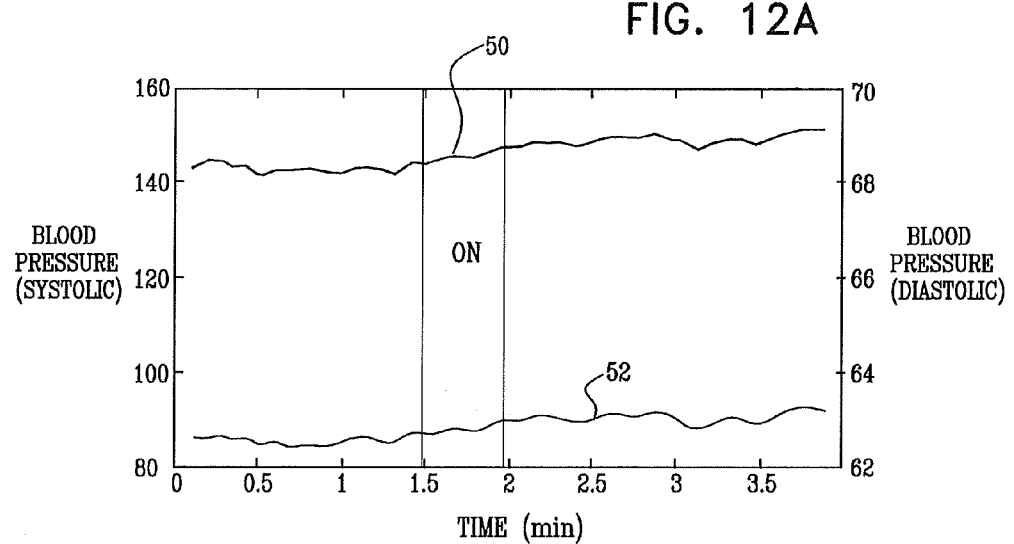
FIGS. 12A-B are graphs showing the effect on a subject's blood pressure of placing devices at respective positions on the subject's internal carotid artery, in accordance with some applications of the present invention.
Figure 12B:
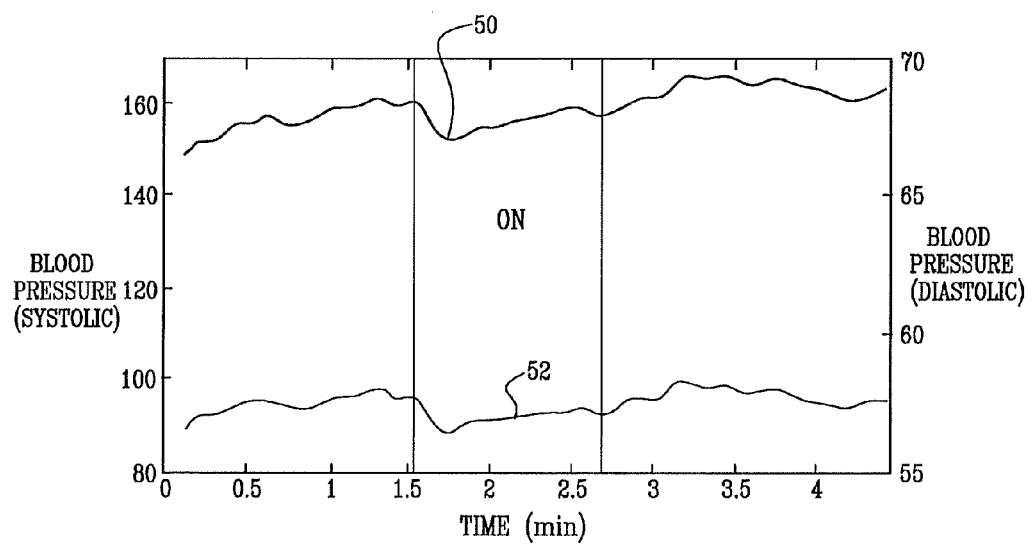

Reference is now made to FIGS. 12A-B, which are graphs showing the effect on blood pressure of placing devices at respective positions on the subject's internal carotid artery, in accordance with some applications of the present invention. The internal carotid artery of a dog was compressed with a surgical needle holder, distally to the carotid sinus, in an area that substantially does not hold any baroreceptors. The systolic and diastolic blood pressures of the dog were measured, and are plotted, respectively, as lines 50 and 52 of FIG. 12A. The compression of the artery started just before 1.5 min, and continued until just before 2 min (i e., between the two vertical lines on FIG. 12A. It may be observed that left internal carotid artery compression at the region that is distal to the carotid sinus did not cause a reduction in blood pressure of the dog. A similar compression technique was used to compress the left carotid sinus, i.e., at an area that is rich with baroreceptors, of a different dog. The systolic and diastolic blood pressures of the dog were measured, and are plotted, respectively, as lines 50 and 52 of FIG. 12B. The compression of the artery started at approximately 1.6 min, and continued until approximately 2.7 min (i.e., between the two vertical lines on FIG. 12B). It may be observed that compression of the dog left carotid sinus did cause blood pressure reduction. These results support one hypothesis of the inventors, which is that a mechanism by which the devices described herein cause a reduction in a subject's blood pressure is by stimulating the subject's baroreceptors.

It is noted that even if not described explicitly, the scope of the present invention includes applying any of the devices described herein to an artery, in accordance with one or more of the following techniques:

(a) The device is attached to the artery while the artery is in an expanded state. The device is attached such that the device maintains the artery in the expanded state. For some applications, the device is attached to the artery such that the effective compliance of the artery is increased by expanding the artery radially. This causes increased baroreceptor stimulation in the artery, by increasing the change in shape that the artery undergoes during the cardiac cycle. Alternatively or additionally, the device increases causes stretching of the baroreceptors by being attached such that the artery is longitudinally stretched.

(b) The device is attached to the artery such that the artery is compressed for at least a portion of the cardiac cycle, relative to when the device is not attached to the artery. Typically, this increases transmural tension in the arterial wall, thereby stimulating baroreceptors.

(c) The device is attached to the artery at a longitudinal site of the artery, such that pressure is applied to the arterial wall at non-contiguous local pressure points around the circumference of the arterial wall. Typically, local pressure points are selected that are identified as being rich in baroreceptors.

(d) For some applications (e.g., when applied to an artery post-surgery), the device uniformly limits expansion of the artery (e.g., during systole) around the circumference of the artery, thereby reducing tension in the arterial wall.

For some applications, the methods and devices described herein are used in combination with the methods and devices described in U.S. Patent Application Publication 2008/0033501 to Gross, and PCT Publication WO 07/013065 to Gross, both of which applications are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An apparatus for stimulating baroreceptors to treat hypertension of a subject, the apparatus comprising:
    a selective circumferential pressure applicator, comprising:
        at least two non-contiguous pressure application surfaces that are configured to increase baroreceptor activity of the subject by applying pressure to an artery of the subject at two or more respective non-contiguous regions around a circumference of the artery at a longitudinal site of the artery, such that between the non-contiguous regions, at the longitudinal site:
            there is at least one region of the artery that is more relaxed than in the absence of the apparatus, and
            there is at least one region of the artery that is more tense than in the absence of the apparatus; and
        a joint configured:
            to couple the at least two surfaces to each other on the circumference of the artery at the longitudinal site, and
            for at least a portion of a cardiac cycle of the subject, not to contact the artery of the subject on the circumference of the artery at the longitudinal site
        wherein the at least two non-contiguous pressure application surfaces and the joint are configured to apply forces passively to the artery during systole and diastole of a cardiac cycle in order to increase the baroreceptor activity and maintain blood flow through the artery.

2. The apparatus according to claim 1, wherein the joint is a rigid joint.

3. The apparatus according to claim 1, wherein the joint is a flexible joint.

4. The apparatus according to claim 1, wherein the at least two-non-contiguous pressure application surfaces are configured to apply the pressure to the artery such that the region of the artery that is more tense is between the joint and the region of the artery that is more relaxed.

5. The apparatus according to claim 1, wherein the at least two-non-contiguous pressure application surfaces are configured to apply the pressure to the artery such that the region of the artery that is more relaxed is between the joint and the region of the artery that is more tense.

6. The apparatus according to claim 1, wherein the at least two non-contiguous pressure application surfaces are slidably coupled to each other.

7. The apparatus according to claim 1, wherein the at least two non-contiguous pressure application surfaces are oriented in general opposition with respect to each other.

8. The apparatus according to claim 7, wherein an angle between two of the at least two surfaces is less than 20 degrees.

9. The apparatus according to claim 8, wherein the angle between two of the at least two surfaces is less than 10 degrees.

10. The apparatus according to claim 1, wherein the at least two non-contiguous pressure application surfaces and the joint are configured to compress the artery and stimulate the baroreceptors without reducing blood flow through the artery.

11. A method for stimulating baroreceptors to treat hypertension of a subject, the method comprising:
    using at least two non-contiguous pressure application surfaces that are coupled to each other by a joint, applying pressure to an outer wall of an artery of the subject at two or more respective non-contiguous regions around a circumference of the artery at a longitudinal site of the artery, such that between the non-contiguous regions, at the longitudinal site:
        there is at least one region of the artery that is more relaxed than in the absence of the at least two non-contiguous pressure application surfaces, and
        there is at least one region of the artery that is more tense than in the absence of the at least two non-contiguous pressure application surfaces, and
    placing the joint such that for at least a portion of a cardiac cycle of the subject the joint does not contact the artery of the subject on the circumference of the artery at the longitudinal site
    wherein the at least two non-contiguous pressure application surfaces and the joint apply forces to the artery passively during systole and diastole of a cardiac cycle in order to stimulate the baroreceptors and maintain blood flow through the artery.

12. The method according to claim 11, wherein applying the pressure comprises applying the pressure to the artery such that the region of the artery that is more tense is between the joint and the region of the artery that is more relaxed.

13. The method according to claim 11, wherein applying the pressure comprises applying the pressure to the artery such that the region of the artery that is more relaxed is between the joint and the region of the artery that is more tense.

14. The method according to claim 11, wherein applying the pressure to the artery comprises applying pressure to the artery at a region of the artery that is rich in baroreceptors.

15. The method according to claim 11, wherein applying the pressure to the artery comprises applying pressure to the artery at a location selected from the group consisting of an upstream location, and a downstream location from a region of the artery that is rich in baroreceptors.

16. The method according to claim 15, further comprising selecting a location as the selected location such that at least a portion of a pressure change induced in the artery at the location, by the at least two surfaces, reaches the region of the artery that is rich in baroreceptors after a time delay from when the pressure change was induced at the location, the time delay being such that baroreceptor stimulation at the region of the artery that is rich in baroreceptors, as a result of the portion of the pressure change that reaches the region of the artery that is rich in baroreceptors, is greater than if the pressure change was induced by the at least two surfaces at the region of the artery that is rich in baroreceptors.

17. The method according to claim 11, wherein applying the pressure to the artery comprises applying the pressure using the at least two non-contiguous pressure application surfaces oriented in general opposition with respect to each other.

18. The method according to claim 17, wherein applying the pressure to the artery comprises applying the pressure using the at least two non-contiguous pressure application surfaces oriented such that an angle between the two surfaces is less than 20 degrees.

19. The method according to claim 18, wherein applying the pressure to the artery comprises applying the pressure using the at least two non-contiguous pressure application surfaces oriented such that the angle between the two surfaces is less than 10 degrees.

20. The method according to claim 11, wherein the at least two non-contiguous pressure application surfaces and the joint compress the artery and stimulate the baroreceptors without reducing blood flow through the artery.

\* \* \* \* \*